United States Patent
Laugero et al.

(10) Patent No.: US 8,309,522 B2
(45) Date of Patent: Nov. 13, 2012

(54) NEUROMEDIN AND FN-38 PEPTIDES FOR TREATING PSYCHIATRIC DISEASES

(75) Inventors: Kevin D. Laugero, Davis, CA (US); Michael R. Hanley, Corte Madero, CA (US); Christine M. Mack, San Diego, CA (US); David G. Parkes, Del Mar, CA (US); Paul McGonigle, Villanova, PA (US)

(73) Assignee: Amylin Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 12/524,903

(22) PCT Filed: Feb. 4, 2008

(86) PCT No.: PCT/US2008/001500
§ 371 (c)(1),
(2), (4) Date: Mar. 11, 2010

(87) PCT Pub. No.: WO2008/097536
PCT Pub. Date: Aug. 14, 2008

(65) Prior Publication Data
US 2010/0168013 A1    Jul. 1, 2010

Related U.S. Application Data

(60) Provisional application No. 60/899,782, filed on Feb. 5, 2007.

(51) Int. Cl.
*A61K 38/00* (2006.01)
(52) U.S. Cl. ............. 514/17.5; 514/17.6; 514/17.7
(58) Field of Classification Search ............. None
See application file for complete search history.

(56) References Cited

U.S. PATENT DOCUMENTS
2003/0211968 A1    11/2003    Liu et al.
2008/0124335 A1    5/2008    Kangawa et al.

FOREIGN PATENT DOCUMENTS
WO    WO 2007/022123    2/2007
WO    WO 2007/075439    7/2007
WO    WO 2007/109135    9/2007

OTHER PUBLICATIONS

Kinkead et al., 2006, CNS & neurological disorders—Drug Targets, 5, pp. 205-218.*
Adams et al., 1997, Peptides, 18, No. 4, 527-35.*
Nabeshima et al., 2006, Ann. N. Y. Acad. Sci., 1086: 160-8.*
Abiko et al., *Amino Acids, Springer Verlag, AU* 25(1):107-110 (Jul. 1, 2003).
Binder et al., *Pharmacological Reviews* 53:453-486 (2001).
Brighton et al., *Mol. Pharmacology* 66 1544-1556 (2004).
Greist et al., *The Merck Manual, 18th Edition*, Chapter 196, pp. 1673-1674, Gary Zelko, Merck Research Laboratories, Whitehouse Stations, NJ, U.S.A. (2006).
Hanada et al., *Biochem and Biophys. Rsch Comm* 289:225-228 (2001).
Hongkui Zeng et al., *Mol. & Cell. Biol.* 26(24):9352-9363 (Oct. 9, 2006).
Shioda et al., *Regulatory Peptides* 145:1-3 (Dec. 20, 2007).
Steckler et al., *Behavioural Pharmacology*, 16(Suppl. 1):S4-S5 (Sep. 2005).

* cited by examiner

*Primary Examiner* — Olga N Chernyshev
(74) *Attorney, Agent, or Firm* — Amylin Pharmaceuticals, LLC

(57) ABSTRACT

Methods and compositions for treating psychiatric diseases and disorders are disclosed. The methods provided generally involve the administration of an NMX peptide, an FNX peptide, or an NMX receptor agonist, or analogs or derivatives thereof, to a subject in order to treat psychiatric diseases and disorders, and conditions associated with psychiatric diseases and disorders.

4 Claims, 4 Drawing Sheets

```
                        SEQUENCE LISTING

<160> NUMBER OF SEQ ID NOS: 76

<210> SEQ ID NO 1
<211> LENGTH: 45
<212> TYPE: PRT
<213> ORGANISM: Homo sapiens

<400> SEQUENCE: 1

Phe Leu Phe His Tyr Ser Lys Thr Gln Lys Leu Gly Lys Ser Asn Val
  1               5                  10                  15

Val Glu Glu Phe Gln Ser Pro Phe Ala Ser Gln Ser Arg Gly Tyr Phe
              20                  25                  30

Leu Phe Arg Pro Arg Asn Gly Arg Arg Ser Ala Gly Phe
          35                  40                  45

<210> SEQ ID NO 2
<211> LENGTH: 36
<212> TYPE: PRT
<213> ORGANISM: Rattus sp.

<400> SEQUENCE: 2

Phe Leu Phe His Tyr Ser Lys Thr Gln Lys Leu Gly Asn Ser Asn Val
  1               5                  10                  15

Val Glu Tyr Gln Gly Pro Val Ala Pro Ser Gly Gly Phe Phe Leu Phe
              20                  25                  30

Arg Pro Arg Asn
          35

<210> SEQ ID NO 3
<211> LENGTH: 38
<212> TYPE: PRT
<213> ORGANISM: Litoria sp.

<400> SEQUENCE: 3

Phe Leu Phe His Tyr Ser Lys Ser His Asp Ser Gly Asn Ser Asp Ile
  1               5                  10                  15

Thr Glu Glu Val Gln Val Pro Gly Gly Val Ile Ser Asn Gly Tyr Phe
              20                  25                  30

Leu Phe Arg Pro Arg Asn
          35

<210> SEQ ID NO 4
<211> LENGTH: 38
<212> TYPE: PRT
<213> ORGANISM: Gallus sp.

<400> SEQUENCE: 4

Phe Leu Phe His Tyr Ser Lys Thr His Asp Ser Gly Asn Ser Asp Val
  1               5                  10                  15

Arg Glu Asp Leu Gln Gly Thr Gly Gly Ile Gln Ser Arg Gly Tyr Phe
              20                  25                  30

Phe Phe Arg Pro Arg Asn
```

<210> SEQ ID NO 5
<211> LENGTH: 38
<212> TYPE: PRT
<213> ORGANISM: Homo sapiens

<400> SEQUENCE: 5

Phe Leu Phe His Tyr Ser Lys Thr Gln Lys Leu Gly Lys Ser Asn Val
1               5                   10                  15

Val Glu Glu Leu Gln Ser Pro Phe Ala Ser Gln Ser Arg Gly Tyr Phe
            20                  25                  30

Leu Phe Arg Pro Arg Asn
        35

<210> SEQ ID NO 6
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Phe Leu Phe His Tyr Ser Lys Thr Gln Lys Leu Gly Lys Ser Asn Val
1               5                   10                  15

Val Glu Glu Leu Gln Ser Pro Phe Ala Ser Gln Ser
            20                  25

<210> SEQ ID NO 7
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Phe Leu Phe His Tyr Ser Lys Thr Gln Lys Leu Gly Lys Ser Asn
1               5                   10                  15

<210> SEQ ID NO 8
<211> LENGTH: 33
<212> TYPE: PRT
<213> ORGANISM: Homo sapiens

<400> SEQUENCE: 8

Ile Leu Gln Arg Gly Ser Gly Thr Ala Ala Val Asp Phe Thr Lys Lys
1               5                   10                  15

Asp His Thr Ala Thr Trp Gly Arg Pro Phe Phe Leu Phe Arg Pro Arg
            20                  25                  30

Asn

<210> SEQ ID NO 9
<211> LENGTH: 36
<212> TYPE: PRT
<213> ORGANISM: Rattus sp.

<400> SEQUENCE: 9

Leu Pro Arg Leu Leu His Thr Asp Ser Arg Met Ala Thr Ile Asp Phe
1               5                   10                  15

Pro Lys Lys Asp Pro Thr Thr Ser Leu Gly Arg Pro Phe Phe Leu Phe

```
                      20                  25                  30

Arg Pro Arg Asn
        35

<210> SEQ ID NO 10
<211> LENGTH: 8
<212> TYPE: PRT
<213> ORGANISM: Porcine sp.

<400> SEQUENCE: 10

Tyr Phe Leu Phe Arg Pro Arg Asn
  1               5

<210> SEQ ID NO 11
<211> LENGTH: 23
<212> TYPE: PRT
<213> ORGANISM: Rattus sp.

<400> SEQUENCE: 11

Tyr Lys Val Asn Glu Tyr Gln Gly Pro Val Ala Pro Ser Gly Gly Phe
  1               5                  10                  15

Phe Leu Phe Arg Pro Arg Asn
              20

<210> SEQ ID NO 12
<211> LENGTH: 9
<212> TYPE: PRT
<213> ORGANISM: Homo sapiens

<400> SEQUENCE: 12

Gly Tyr Phe Leu Phe Arg Pro Arg Asn
  1               5

<210> SEQ ID NO 13
<211> LENGTH: 23
<212> TYPE: PRT
<213> ORGANISM: Litoria sp.

<400> SEQUENCE: 13

Ser Asp Glu Glu Val Gln Val Pro Gly Gly Val Ile Ser Asn Gly Tyr
  1               5                  10                  15

Phe Leu Phe Arg Pro Arg Asn
              20

<210> SEQ ID NO 14
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Phe Leu Phe His Tyr Ser Lys Thr Gln Lys Leu Gly Lys Ser Asn Ser
  1               5                  10                  15

Asp Glu Glu Val Gln Val Pro Gly Gly Val Ile Ser Asn Gly Tyr Phe
              20                  25                  30

Leu Phe Arg Pro Arg Asn
        35

<210> SEQ ID NO 15
<211> LENGTH: 30
<212> TYPE: PRT
```

-continued

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Phe Leu Phe His Tyr Ser Lys Thr Gln Lys Leu Gly Lys Ser Asn Ser
  1               5                  10                  15

Asp Glu Glu Val Gln Val Pro Gly Gly Val Ile Ser Asn Gly
             20                  25                  30

<210> SEQ ID NO 16
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Phe Leu Phe His Tyr Ser Lys Thr Gln Lys Leu Gly Lys Ser Asn Val
  1               5                  10                  15

Val Glu Glu Leu Gln Ser Pro Phe Ala Ser Gln Ser Arg Gly
             20                  25                  30

<210> SEQ ID NO 17
<211> LENGTH: 25
<212> TYPE: PRT
<213> ORGANISM: Homo sapiens

<400> SEQUENCE: 17

Phe Arg Val Asp Glu Glu Phe Gln Ser Pro Phe Ala Ser Gln Ser Arg
  1               5                  10                  15

Gly Tyr Phe Leu Phe Arg Pro Arg Asn
             20                  25

<210> SEQ ID NO 18
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Tyr Phe Leu Phe Arg Pro Arg Asn
  1               5

<210> SEQ ID NO 19
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Tyr Phe Leu Tyr Arg Pro Arg Asn
  1               5

<210> SEQ ID NO 20
<211> LENGTH: 8
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Tyr Phe Val Phe Arg Pro Arg Asn
 1               5

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Phe Phe Leu Phe Arg Pro Arg Asn
 1               5

<210> SEQ ID NO 22
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Tyr Phe Leu Val Arg Pro Arg Asn
 1               5

<210> SEQ ID NO 23
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Tyr Phe Phe Phe Arg Pro Arg Asn
 1               5

<210> SEQ ID NO 24
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Tyr Phe Leu Phe His Pro Arg Asn
 1               5

<210> SEQ ID NO 25
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 25

Tyr Phe Leu Phe Arg Pro His Asn
  1               5

<210> SEQ ID NO 26
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Tyr Phe Leu Phe Arg
  1               5

<210> SEQ ID NO 27
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Phe Phe Phe Tyr His Pro His Asn
  1               5

<210> SEQ ID NO 28
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Phe Phe Phe Phe Arg Pro Arg Asn
  1               5

<210> SEQ ID NO 29
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Phe Phe Phe Phe Lys His His Asn
  1               5

<210> SEQ ID NO 30
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Phe Phe Phe Phe Lys
  1               5
```

<210> SEQ ID NO 31
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 31

Phe Leu Phe His Tyr Ser Lys Thr Gln Lys Leu Gly Lys Ser Asn Val
 1               5                  10                  15

Val Glu Glu Leu Gln Ser Pro Phe Ala Ser Gln Ser Arg Gly Phe Phe
            20                  25                  30

Leu Phe Arg Pro Arg Asn
        35

<210> SEQ ID NO 32
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 32

Phe Leu Phe His Tyr Ser Lys Thr Gln Lys Leu Gly Lys Ser Asn Val
 1               5                  10                  15

Val Glu Glu Leu Gln Ser Pro Phe Ala Ser Gln Ser Arg Gly Tyr Phe
            20                  25                  30

Leu Val Arg Pro Arg Asn
        35

<210> SEQ ID NO 33
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 33

Phe Leu Phe His Tyr Ser Lys Thr Gln Lys Leu Gly Lys Ser Asn Val
 1               5                  10                  15

Val Glu Glu Leu Gln Ser Pro Phe Ala Ser Gln Ser Arg Gly Tyr Phe
            20                  25                  30

Phe Phe Arg Pro Arg Asn
        35

<210> SEQ ID NO 34
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 34

Phe Leu Phe His Tyr Ser Lys Thr Gln Lys Leu Gly Lys Ser Asn Val
 1               5                  10                  15

Val Glu Glu Leu Gln Ser Pro Phe Ala Ser Gln Ser Arg Gly Tyr Phe

Leu Phe His Pro Arg Asn
        35

<210> SEQ ID NO 35
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Phe Leu Phe His Tyr Ser Lys Thr Gln Lys Leu Gly Lys Ser Asn Val
 1               5                  10                  15

Val Glu Glu Leu Gln Ser Pro Phe Ala Ser Gln Ser Arg Gly Tyr Phe
            20                  25                  30

Leu Phe Arg Pro His Asn
        35

<210> SEQ ID NO 36
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Phe Leu Phe His Tyr Ser Lys Thr Gln Lys Leu Gly Lys Ser Asn Val
 1               5                  10                  15

Val Glu Glu Leu Gln Ser Pro Phe Ala Ser Gln Ser Arg Gly Tyr Phe
            20                  25                  30

Leu Phe Arg
        35

<210> SEQ ID NO 37
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Phe Leu Phe His Tyr Ser Lys Thr Gln Lys Leu Gly Lys Ser Asn Val
 1               5                  10                  15

Val Glu Glu Leu Gln Ser Pro Phe Ala Ser Gln Ser Arg Gly Phe Phe
            20                  25                  30

Phe Tyr His Pro His Asn
        35

<210> SEQ ID NO 38
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Phe Leu Phe His Tyr Ser Lys Thr Gln Lys Leu Gly Lys Ser Asn Val
1               5                   10                  15

Val Glu Glu Leu Gln Ser Pro Phe Ala Ser Gln Ser Arg Gly Phe Phe
            20                  25                  30

Phe Phe Arg Pro Arg Asn
        35

<210> SEQ ID NO 39
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Phe Leu Phe His Tyr Ser Lys Thr Gln Lys Leu Gly Lys Ser Asn Val
1               5                   10                  15

Val Glu Glu Leu Gln Ser Pro Phe Ala Ser Gln Ser Arg Gly Phe Phe
            20                  25                  30

Phe Phe Lys His His Asn
        35

<210> SEQ ID NO 40
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Phe Leu Phe His Tyr Ser Lys Thr Gln Lys Leu Gly Lys Ser Asn Val
1               5                   10                  15

Val Glu Glu Leu Gln Ser Pro Phe Ala Ser Gln Ser Arg Gly Phe Phe
            20                  25                  30

Phe Phe Lys
        35

<210> SEQ ID NO 41
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Phe Leu Phe His Tyr Ser Lys Thr Gln Lys Leu Gly Lys Ser Asn Ser
1               5                   10                  15

Asp Glu Glu Val Gln Val Pro Gly Gly Val Ile Ser Asn Gly Phe Phe
            20                  25                  30

Leu Phe Arg Pro Arg Asn
        35

<210> SEQ ID NO 42
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic peptide"

<400> SEQUENCE: 42

Phe Leu Phe His Tyr Ser Lys Thr Gln Lys Leu Gly Lys Ser Asn Ser
1               5                   10                  15

Asp Glu Glu Val Gln Val Pro Gly Gly Val Ile Ser Asn Gly Tyr Phe
            20                  25                  30

Leu Val Arg Pro Arg Asn
        35

<210> SEQ ID NO 43
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Phe Leu Phe His Tyr Ser Lys Thr Gln Lys Leu Gly Lys Ser Asn Ser
1               5                   10                  15

Asp Glu Glu Val Gln Val Pro Gly Gly Val Ile Ser Asn Gly Tyr Phe
            20                  25                  30

Phe Phe Arg Pro Arg Asn
        35

<210> SEQ ID NO 44
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Phe Leu Phe His Tyr Ser Lys Thr Gln Lys Leu Gly Lys Ser Asn Ser
1               5                   10                  15

Asp Glu Glu Val Gln Val Pro Gly Gly Val Ile Ser Asn Gly Tyr Phe
            20                  25                  30

Leu Phe His Pro Arg Asn
        35

<210> SEQ ID NO 45
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Phe Leu Phe His Tyr Ser Lys Thr Gln Lys Leu Gly Lys Ser Asn Ser
1               5                   10                  15

Asp Glu Glu Val Gln Val Pro Gly Gly Val Ile Ser Asn Gly Tyr Phe
            20                  25                  30

Leu Phe Arg Pro His Asn
        35

<210> SEQ ID NO 46
<211> LENGTH: 35
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Phe Leu Phe His Tyr Ser Lys Thr Gln Lys Leu Gly Lys Ser Asn Ser
 1               5                  10                  15

Asp Glu Glu Val Gln Val Pro Gly Gly Val Ile Ser Asn Gly Tyr Phe
            20                  25                  30

Leu Phe Arg
         35

<210> SEQ ID NO 47
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Phe Leu Phe His Tyr Ser Lys Thr Gln Lys Leu Gly Lys Ser Asn Ser
 1               5                  10                  15

Asp Glu Glu Val Gln Val Pro Gly Gly Val Ile Ser Asn Gly Phe Phe
            20                  25                  30

Phe Tyr His Pro His Asn
         35

<210> SEQ ID NO 48
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Phe Leu Phe His Tyr Ser Lys Thr Gln Lys Leu Gly Lys Ser Asn Ser
 1               5                  10                  15

Asp Glu Glu Val Gln Val Pro Gly Gly Val Ile Ser Asn Gly Phe Phe
            20                  25                  30

Phe Phe Arg Pro Arg Asn
         35

<210> SEQ ID NO 49
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Phe Leu Phe His Tyr Ser Lys Thr Gln Lys Leu Gly Lys Ser Asn Ser
 1               5                  10                  15

Asp Glu Glu Val Gln Val Pro Gly Gly Val Ile Ser Asn Gly Phe Phe
            20                  25                  30

Phe Phe Lys His His Asn
         35
```

```
<210> SEQ ID NO 50
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Phe Leu Phe His Tyr Ser Lys Thr Gln Lys Leu Gly Lys Ser Asn Ser
 1               5                  10                  15

Asp Glu Glu Val Gln Val Pro Gly Gly Val Ile Ser Asn Gly Phe Phe
            20                  25                  30

Phe Phe Lys
         35

<210> SEQ ID NO 51
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Phe Leu Phe His Tyr Ser Lys Thr Gln Lys Leu Gly Lys Ser Asn Glu
 1               5                  10                  15

Glu Leu Gln Ser Pro Phe Ala Ser Gln Ser Arg Gly Tyr Phe Leu Phe
            20                  25                  30

Arg Pro Arg Asn
         35

<210> SEQ ID NO 52
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Phe Leu Phe His Tyr Ser Lys Thr Gln Lys Leu Gly Lys Ser Asn Val
 1               5                  10                  15

Val Glu Glu Leu Gln Ser Pro Ser Arg Gly Tyr Phe Leu Phe Arg Pro
            20                  25                  30

Arg Asn

<210> SEQ ID NO 53
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Phe Leu Phe His Tyr Ser Lys Thr Gln Lys Leu Gly Lys Ser Asn Glu
 1               5                  10                  15

Glu Leu Gln Ser Pro Ser Arg Gly Tyr Phe Leu Phe Arg Pro Arg Asn
            20                  25                  30
```

```
<210> SEQ ID NO 54
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Tyr Ser Lys Thr Gln Lys Leu Gly Lys Ser Asn Val Val Glu Glu Leu
 1               5                  10                  15

Gln Ser Pro Phe Ala Ser Gln Ser Arg Gly Tyr Phe Leu Phe Arg Pro
            20                  25                  30

Arg Asn

<210> SEQ ID NO 55
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Phe Leu Phe His Tyr Lys Leu Gly Lys Ser Asn Val Val Glu Glu Leu
 1               5                  10                  15

Gln Ser Pro Phe Ala Ser Gln Ser Arg Gly Tyr Phe Leu Phe Arg Pro
            20                  25                  30

Arg Asn

<210> SEQ ID NO 56
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Phe Leu Phe His Tyr Ser Lys Thr Gln Lys Leu Gly Leu Gln Ser Pro
 1               5                  10                  15

Phe Ala Ser Gln Ser Arg Gly Tyr Phe Leu Phe Arg Pro Arg Asn
            20                  25                  30

<210> SEQ ID NO 57
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Phe Gln Lys Leu Gly Lys Ser Asn Val Val Glu Glu Leu Gln Ser Pro
 1               5                  10                  15

Phe Ala Ser Gln Ser Arg Gly Tyr Phe Leu Phe Arg Pro Arg Asn
            20                  25                  30

<210> SEQ ID NO 58
<211> LENGTH: 21
<212> TYPE: PRT
```

<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 58

Phe Leu Phe His Tyr Ser Phe Ala Ser Gln Ser Arg Gly Tyr Phe Leu
 1               5                  10                  15

Phe Arg Pro Arg Asn
            20

<210> SEQ ID NO 59
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 59

Phe Leu Phe His Tyr Ser Lys Thr Gln Lys Leu Gly Lys Ser Asn Gly
 1               5                  10                  15

Tyr Phe Leu Phe Arg Pro Arg Asn
            20

<210> SEQ ID NO 60
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 60

Phe Leu Phe His Tyr Ser Lys Thr Gln Lys Leu Gly Lys Ser Asn Ser
 1               5                  10                  15

Arg Gly Tyr Phe Leu Phe Arg Pro Arg Asn
            20                  25

<210> SEQ ID NO 61
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 61

Phe Leu Phe His Tyr Ser Lys Thr Gln Lys Leu Gly Lys Ser Asn Glu
 1               5                  10                  15

Glu Leu Gln Ser Pro Ser Arg Gly Tyr Phe Leu Phe Lys Pro Arg Asn
            20                  25                  30

<210> SEQ ID NO 62
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 62

Phe Leu Phe His Tyr Ser Gly Tyr Phe Leu Phe Arg Pro Arg Asn
 1               5                  10                  15

<210> SEQ ID NO 63
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Lys Leu Gly Lys Ser Asn Val Val Glu Glu Leu Gln Ser Pro Phe Ala
 1               5                  10                  15

Ser Gln Ser Arg Gly Tyr Phe Leu Phe Arg Pro Arg Asn
            20                  25

<210> SEQ ID NO 64
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Tyr Ser Lys Thr Gln Lys Leu Gly Lys Ser Asn Glu Glu Leu Gln Ser
 1               5                  10                  15

Pro Ser Arg Gly Tyr Phe Leu Phe Arg Pro Arg Asn
            20                  25

<210> SEQ ID NO 65
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Phe Leu Phe His Tyr Ser Gly Tyr Phe Leu Phe Arg
 1               5                  10

<210> SEQ ID NO 66
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Phe Leu Phe His Tyr Ser Gly Phe Phe Leu Phe Arg
 1               5                  10

<210> SEQ ID NO 67
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Phe Leu Phe His Tyr Ser Gly Tyr Phe Leu Phe Lys Pro Arg Asn
 1               5                  10                  15

<210> SEQ ID NO 68
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Phe Leu Phe His Tyr Ser Gly Phe Phe Leu Phe Arg Pro Arg Asn
 1               5                  10                  15

<210> SEQ ID NO 69
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Phe Leu Phe His Tyr Ser Gly Phe Phe Leu Phe Lys Pro Arg Asn
 1               5                  10                  15

<210> SEQ ID NO 70
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Phe Leu Phe His Tyr Ser Lys Thr Gln Lys Leu Gly Lys Ser Asn Glu
 1               5                  10                  15

Glu Val Gln Val Pro Gly Gly Val Ile Ser Asn Gly Tyr Phe Leu Phe
                 20                  25                  30

Arg Pro Arg Asn
         35

<210> SEQ ID NO 71
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Phe Leu Phe His Tyr Ser Lys Thr Gln Lys Leu Gly Lys Ser Asn Ser
 1               5                  10                  15

Asp Glu Glu Val Gln Val Pro Ser Asn Gly Tyr Phe Leu Phe Arg Pro
                 20                  25                  30

Arg Asn

<210> SEQ ID NO 72
<211> LENGTH: 32
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 72

Phe Leu Phe His Tyr Ser Lys Thr Gln Lys Leu Gly Lys Ser Asn Glu
1               5                   10                  15

Glu Val Gln Val Pro Ser Asn Gly Tyr Phe Leu Phe Arg Pro Arg Asn
            20                  25                  30

<210> SEQ ID NO 73
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Tyr Ser Lys Thr Gln Lys Leu Gly Lys Ser Asn Val Val Glu Glu Leu
1               5                   10                  15

Gln Ser Pro Phe Ala Ser Gln Ser Arg Gly Tyr Phe Leu Phe Arg Pro
            20                  25                  30

Arg Asn

<210> SEQ ID NO 74
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Phe Leu Phe His Tyr Lys Leu Gly Lys Ser Asn Val Val Glu Glu Leu
1               5                   10                  15

Gln Ser Pro Phe Ala Ser Gln Ser Arg Gly Tyr Phe Leu Phe Arg Pro
            20                  25                  30

Arg Asn

<210> SEQ ID NO 75
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Phe Leu Phe His Tyr Ser Lys Thr Gln Lys Leu Gly Val Gln Val Pro
1               5                   10                  15

Gly Gly Val Ile Ser Asn Gly Tyr Phe Leu Phe Arg Pro Arg Asn
            20                  25                  30

<210> SEQ ID NO 76
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 76

Phe Gln Lys Leu Gly Lys Ser Asn Ser Asp Glu Glu Val Gln Val Pro
 1               5                  10                  15

Gly Gly Val Ile Ser Asn Gly Tyr Phe Leu Phe Arg Pro Arg Asn
                20                  25                  30
```

NEUROMEDIN AND FN-38 PEPTIDES FOR TREATING PSYCHIATRIC DISEASES

Figure 1:
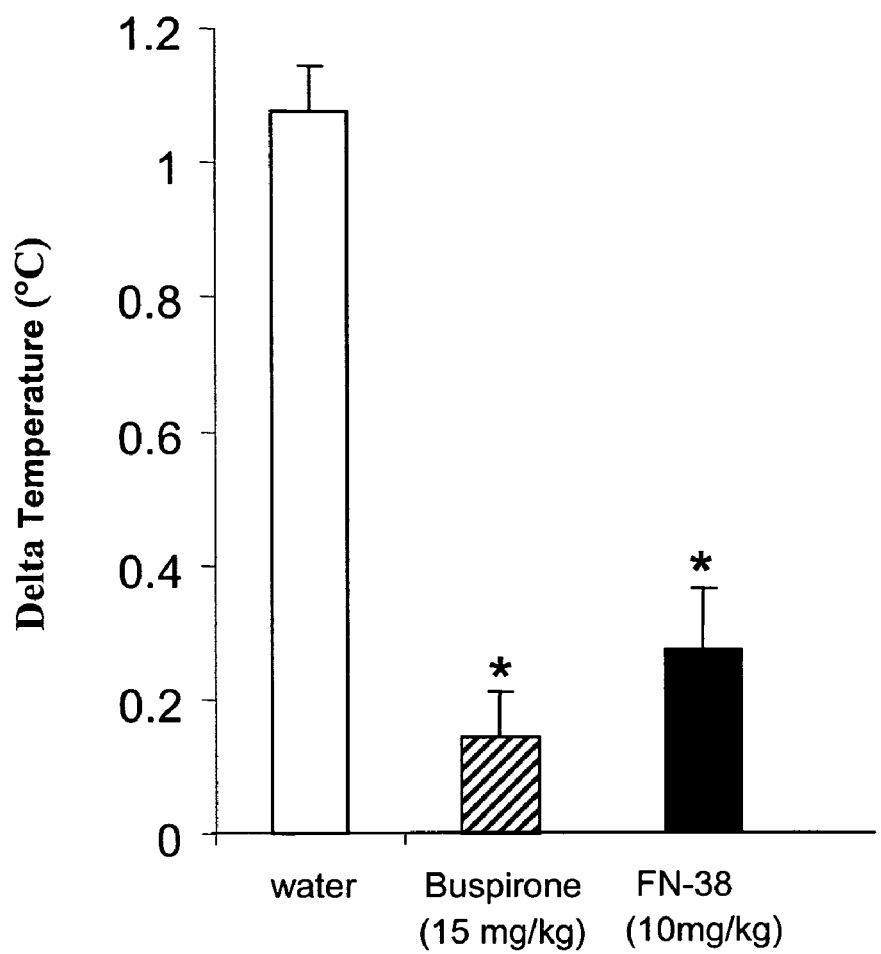

This application is a 371 of PCT/US2008/001500 filed Feb. 4, 2008, which claims priority to U.S. Application No. 60/899,782 filed Feb. 5, 2007.

TECHNICAL FIELD

This disclosure is in the medical field and in particular to the fields of psychology and psychiatry, as well as health, diet and nutrition.

BACKGROUND

Psychiatric diseases and disorders (also referred to as mental illnesses or disorders) are described in resources such as the American Psychiatric Association's *Diagnostic and Statistical Manual of Mental Disorders* (DSM-IV). Broad categories of mental disorders include, but are not limited to, mood disorders, anxiety disorders, schizophrenia and other psychotic disorders, substance-related disorders, sleep disorders, somatoform disorders, and eating disorders. Examples of mood disorders include bipolar and depression. Other conditions falling within the broader category of disorders described above can be found in the DSM-IV, which is incorporated by reference in its entirety and for all purposes. These are debilitating illnesses that affect millions of people and involve astronomical costs, in terms of treatment, lost productivity, and emotional toll.

In 2001, the National Institute of Mental Health published a summary of statistics describing the prevalence of mental disorders in America. In the report, it estimated that 22.1% of Americans ages 18 and older suffer from a diagnosable mental disorder in a given year (Reiger et al., 1993, *Archives of General Psychiatry* 50:85-94). When applied to the 1998 U.S. Census, the number of people affected was 44.3 million.

Depressive disorders can encompass, among others illnesses, major depressive disorder, dysthymic disorder and bipolar disorder. About 9 to 9.5 percent of the U.S. population ages 18 and older have a depressive condition. It has been reported that the direct cost of depressive disorders is about $80 billion, with two-thirds of it being borne by businesses. The indirect costs associated with depressive disorders, such as lost productivity, are harder to calculate because of events such as "presenteeism," described as people at work but limited in their ability to produce or participate (Durso, *Employee Benefit News*, December, 2004).

Another psychiatric condition is anxiety disorders. These disorders can include panic disorder, obsessive-compulsive disorder, post-traumatic stress disorder generalized anxiety disorder, and phobias. Approximately 19.1 million American adults ages 18 to 54 (about 13.3% of people in this age group in a given year) have an anxiety disorder.

Another common psychiatric condition is eating disorders. There are three main types, anorexia nervosa, bulimia nervosa, and binge-eating disorders. These psychiatric conditions are often linked to perceived notions relating to body image and are usually independent of actual body weight or body mass index. The mortality of people with anorexia has been estimated at 0.56 percent per year, or approximately 5.6 percent per decade, which is about 12 times higher than the annual death rate due to all causes of death among females ages 15-24 in the general population (Sullivan, 1995, *American Journal of Psychiatry* 152:1073-1074). It should be noted that psychiatric illnesses usually present with elements of other psychiatric disorders.

Another psychiatric condition is schizophrenia. In a given year, over 2 million people are clinically diagnosed with schizophrenia, and there is a lifetime prevalence of this disease in approximately 1% of the U.S. population. Schizophrenia is a chronic, debilitating disease that leaves an estimated 75% of treated patients without ever achieving complete recovery. Treatment of schizophrenia with the newer (atypical) antipsychotic medications frequently comes with the side effect of weight gain and possibly diabetes.

Exemplary types of schizophrenia include paranoid schizophrenia. These persons are very suspicious of others and often have grand schemes of persecution at the root of their behavior. Hallucinations, and more frequently delusions, are a prominent and common part of the illness. Persons with disorganized schizophrenia (hebephrenic schizophrenia) are verbally incoherent and may have moods and emotions that are not appropriate to the situation. Hallucinations are not usually present with disorganized schizophrenia. Catatonic schizophrenia describes where a person is extremely withdrawn, negative and isolated, and has marked psychomotor disturbances. Residual schizophrenia describes where a person is not currently suffering from delusions, hallucinations, or disorganized speech and behavior, but lacks motivation and interest in day-to-day living. Schizoaffective disorder describes where a person has symptoms of schizophrenia as well as mood disorder such as major depression, bipolar mania, or mixed mania. Undifferentiated schizophrenia describes where conditions meet the general diagnostic criteria for schizophrenia but do not conform to any of the above subtypes, or there are features of more than one of the subtypes without a clear predominance of a particular set of diagnostic characteristics.

Psychiatric diseases and disorders can be found in any age group. Accordingly, these disorders can be found in young adults and adults (defined herein as those aged 65 or under) as well as infants, children, adolescents, and the elderly (defined herein as over the age of 65). In fact, certain segments of the population may be particularly prone to having a condition, such as eating disorders in adolescents and young adults. The elderly may be particularly susceptible to conditions such as depression.

Current treatments include psychosocial and behavioral therapy, electroconvulsive therapy, and/or medication. A common form of treatment for psychiatric illnesses, or at least a component of the treatment, is the administration of medication. A need remains for new and/or improved molecules and medications effective to treat psychiatric diseases and disorders. In addition, needed are molecules that effectively treat those patients resistant to the current medications, effectively treat psychiatric diseases or disorders without the unwanted side effects of the current medications, have a faster onset of therapeutic action, and/or improve physical co-morbidities (e.g., diabetes, pain, weight gain) that often present with and make more difficult the treatment of psychiatric illnesses.

All references cited herein are incorporated by reference in their entirety and for all purposes.

SUMMARY

In a first aspect, methods provided include the use of an NMX peptide, an FNX peptide, or an NMX receptor agonist, or an analog or a derivative thereof, in a therapeutically effective amount for the treatment of a psychiatric disorder. In certain embodiments, the psychiatric disorder is an anxiety disorder, schizophrenia or other psychotic disorder. In certain embodiments, the psychiatric disorder is an obsessive-compulsive disorder. In certain embodiments, NMX peptides, FNX peptides, or NMX receptor agonists, or analogs or derivatives thereof, are used to treat the underlying psychiatric condition of an eating disorder.

In another aspect, methods provided herein include administration of a therapeutically effective amount of an NMX peptide, an FNX peptide, or an NMX receptor agonist, or an analog or a derivative thereof, in combination with a conventional treatment for psychiatric disorders, to a subject in need thereof. In certain embodiments, the combination includes the administration of electroconvulsive therapy (ECT). In other embodiments, the combination includes the administration of at least one other medication for treating a psychiatric disease or disorder. In still other embodiments, the at least one other medication for treating a psychiatric disease or disorder is one or more of tricyclic antidepressants, monoamine oxidase inhibitors (MAOIs), selective serotonin reuptake inhibitors (SSRIs), serotonin and noradrenaline reuptake inhibitors (SNRIs), herbal antidepressants (e.g., St John's Wort or hypericum), or second generation antipsychotic medications (SGAs). In some embodiments, the combination includes the administration of an amylin or its agonists, analogs, or derivatives, as the at least one other medication for treating a psychiatric disease or disorder. In some embodiments, the at least one other medication for treating a psychiatric disease or disorder is not an amylin or its agonists, analogs, or derivatives.

In another aspect, methods provided herein include treating an unwanted side effect of another psychiatric medication comprising administering a therapeutically effective amount of an NMX peptide, an FNX peptide, or an NMX receptor agonist, or an analog or a derivative thereof, to a subject in need thereof. In certain embodiments, the other psychiatric medication is an SGA medication. In certain embodiments, the unwanted side effect of the other psychiatric medication is weight gain. In other embodiments, the unwanted side effect of the other psychiatric medication is diabetes.

In another aspect, methods provided include treating a psychiatric disorder in a subject desirous of, or in need of, treatment comprising administering a therapeutically effective amount of an NMX peptide, an FNX peptide, or an NMX receptor agonist, or an analog or a derivative thereof, to the subject. In certain embodiments, the subject is overweight. In other embodiments, the subject is obese. In still other embodiments, the subject is lean, not overweight or obese. In still other embodiments, the subject has a metabolic condition. In yet other embodiments, the subject has diabetes, metabolic syndrome, impaired glucose tolerance, or insulin resistance.

In another aspect, methods provided include treating a psychiatric disorder comprising administering a therapeutically effective amount of a compound that modulates behavioral pathways through its modulatory actions on metabolic pathways or function. In certain embodiments, the behavioral pathway is the $5HT_{1A}$ pathway or any pathway comprising the serotonergic system. In certain embodiments, the behavioral pathway is stress responsive. In certain embodiments, the compound is an NMX peptide, an FNX peptide, or an NMX receptor agonist, or an analog or a derivative thereof.

In another aspect, the disclosure provides for the use of an NMX peptide, an FNX peptide, or an NMX receptor agonist, or an analog or a derivative thereof, for manufacture of a medicament useful for treating psychiatric diseases and disorders described herein. In yet another aspect, the disclosure provides for the use of an NMX peptide, an FNX peptide, or an NMX receptor agonist, or an analog or a derivative thereof, for manufacture of a medicament useful for treating unwanted side effects of another psychiatric medication, for example without limitation, an SGA. Further to any aspect or embodiment described herein, additionally contemplated is the use of a compound described herein for manufacture of a medicament useful for treating psychiatric diseases and disorders, wherein in certain embodiments, the psychiatric disorder is an anxiety disorder, schizophrenia or other psychotic disorder.

BRIEF DESCRIPTIONS OF THE DRAWINGS

FIG. 1 depicts the effect of FN-38 (SEQ ID NO:5) and control agents on stress-induced hyperthermia in mice, as described in Example 2. Legend: Water (open); buspirone, 15 mg/kg (striped); FN-38 (filled).

Figure 2:
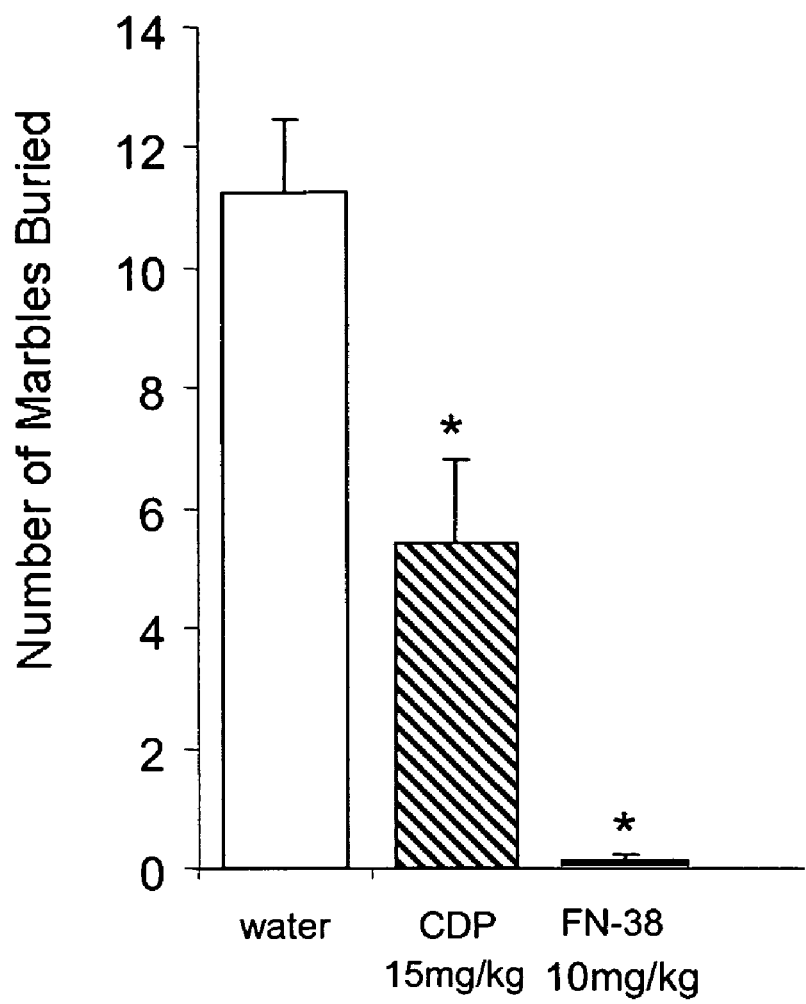

FIG. 2 depicts the effect of FN-38 (SEQ ID NO:5) and control agents on marble burying, as described in Example 2. Legend: Water (open); chlordiazepoxide (CDP) (striped); FN-38 (filled).

Figure 3:
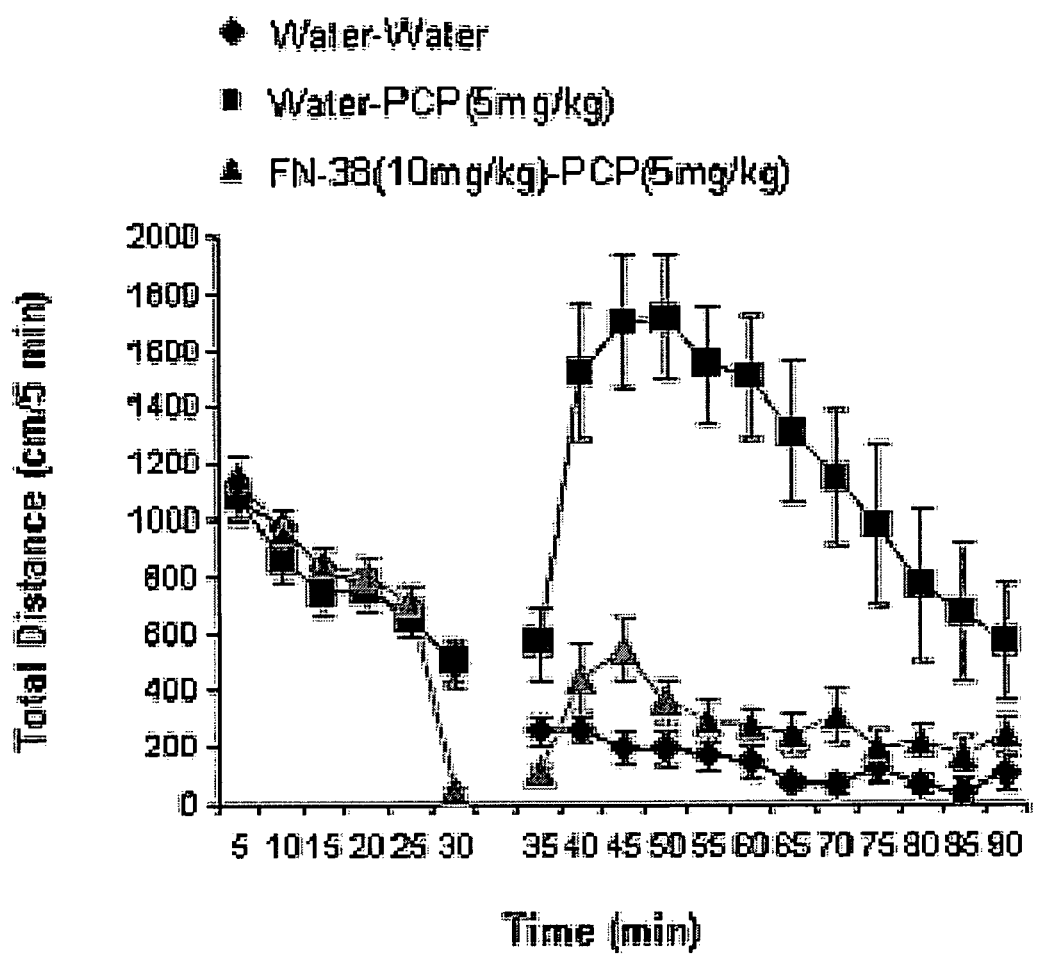

FIG. 3 depicts the effect of FN-38 (SEQ ID NO:5) and control agents on phencyclidine (PCP)-induced locomotion, as described in Example 2. Legend (initial-subsequent injection contents): water-water (diamonds); water-PCP (boxes); FN-38-PCP (triangles).

Figure 4:
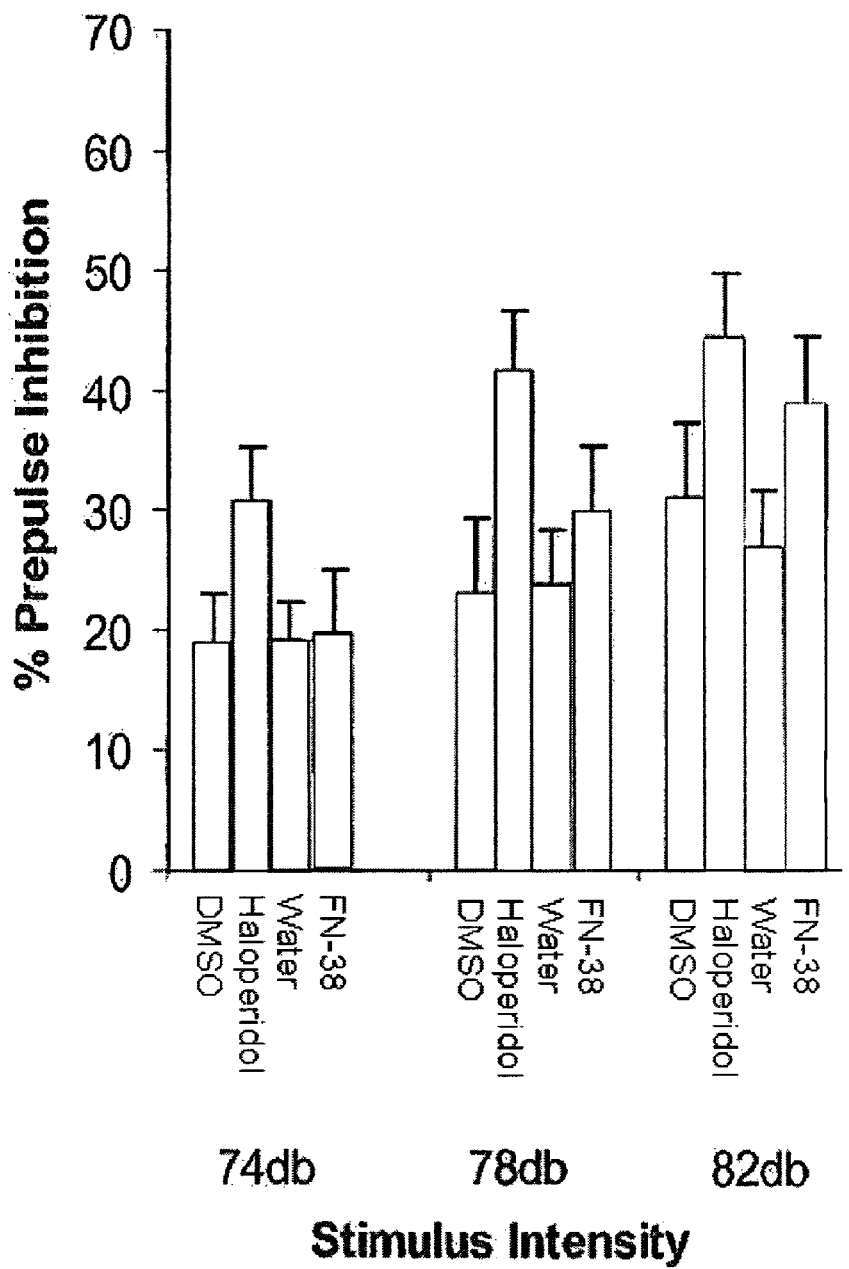

FIG. 4 depicts the effect of 10 mg/kg FN-38 (SEQ ID NO:5) and control agents on prepulse inhibition at the prepulse stimulus intensities of 74, 78, and 82 dB, as described in Example 2.

DETAILED DESCRIPTION

It has now been discovered that an NMX peptide, an FNX peptide, or an NMX receptor agonist, or an analog or a derivative thereof, or a combination thereof, present novel pharmacotherapeutic options. For example as demonstrated herein, compound FN-38 (FLFHYSKTQKLGKSNVVEELQSPFASQSRGYFLFRPRN, SEQ ID NO:5) amide is shown to share properties of anxiolytic and antipsychotic agents in behavioral testing. "FN-38 peptide" and like terms refer to FN-38 and analogs based thereon. Administration of FN-38 to animals results in behavioral effects that include anti-stress, anxiolytic, and antipsychotic actions. Thus, an NMX peptide, an FNX peptide, or an NMX receptor agonist, or an analog or a derivative thereof, may have the surprising ability to treat psychiatric disorders. Psychiatric disorders that can be treated include anxiety disorders and schizophrenia and other psychotic disorders. These compounds may be particularly effective in treating psychiatric disorders that have elements of metabolic disturbances, e.g., in treating subjects with a psychiatric disorder or those with a psychiatric disorder and who also suffer from a metabolic disturbance. More particular types of the above named disorders can be found in the DSM-IV. The following are examples without limitation of disorders that may be treated by the methods disclosed herein.

In some embodiments, methods provided can be used to treat subjects with anxiety disorder. Examples include anxiety disorders can include panic disorder, specific phobia, social phobia, obsessive-compulsive disorder, posttraumatic stress disorder, acute stress disorder, generalized anxiety disorder, anxiety disorder due to a medical condition, substance-induced anxiety disorder and anxiety disorder not otherwise specified.

In some embodiments, methods provided can be used to treat subjects with schizophrenia and other psychotic disorders. Schizophrenia and other psychotic disorders feature a mixture of generally characteristic signs and symptoms, both positive and negative. Positive symptoms of schizophrenia and other psychotic disorders appear to reflect an excess or distortion of normal functions, whereas the negative symptoms appear to reflect a diminution or loss of normal functions. Positive symptoms include, but are not limited to, delusions, hallucinations, disorganized thinking or thought disorder, grossly disorganized behavior, and catatonic motor behavior. Positive symptoms may comprise two distinct dimensions: the "psychotic dimension" includes delusions and hallucinations and the "disorganization dimension" includes disorganized speech and behavior. Negative symptoms include, but are not limited to, affective flattening, alogia, and avolition. Affective flattening is generally displayed as restrictions in the range and intensity of emotional expression. Alogia is generally displayed as restrictions in the fluency and productivity of thought and speech. Avolition is generally displayed as restrictions in the initiation of goal-directed behavior.

Schizophrenia and other psychotic disorders include schizophrenia, schizophreniform disorder, schizoaffective disorder, delusional disorder, brief psychotic disorder, shared psychotic disorder, psychotic disorder due to a general medical condition, substance-induced psychotic disorder and psychotic disorder not otherwise specified. Schizoaffective disorder involves characteristic symptoms of schizophrenia and a major depressive, manic, or mixed depressive and manic episode.

In some instances, a psychiatric disorder may result from use of a particular substance or drug. In some embodiments, methods provided include the treatment of subjects with substance-induced psychiatric disorders. Substance-induced anxiety disorder can occur in response to substances which include, but are not limited to, caffeine, cannabis, cocaine, hallucinogens, amphetamines, phencyclidines, phencyclidine-like substances, and inhalants. Substance-induced psychotic disorder can occur in response to substances which include, but are not limited to, cocaine, hallucinogens, narcotics, opioids, amphetamines, phencyclidines, phencyclidine-like substances, and inhalants. Substance-related disorders can occur in response to one substance or to a combination of substances, such as in polysubstance-related disorder.

In some instances, the psychiatric disorder may result from medication for or treatment of a different disease (other than the psychiatric disease). Accordingly, in some embodiments, methods for treating medication-induced psychiatric disorders or psychiatric disorders that result from treatment of a disease in a subject are provided. In some embodiments, methods provided include the treatment of medication-induced anxiety disorders or medication-induced psychotic disorders that result from treatment of a disease. In some embodiments, methods provided include the treatment of anxiety or anxiousness associated with taking a medication, such as, a prescription medication, an over-the-counter medication, or an herbal remedy or medication. For example, psychiatric side-effects such as anxiety, depression, and psychosis are commonly associated with interferon therapy in patients with chronic hepatitis C disease (Kraus et al., 2005, *World J. Gastroenterol.* 11:1769-1774; Neri et al., 2006, *Clin. Drug Investig.* 26:655-662).

In some embodiments, methods provided can be used to treat subjects with personality disorders, including, but not limited to, schizoid personality disorder and schizotypal personality disorder. Individuals with schizoid personality disorder may also experience symptoms of depression and/or transient psychotic episodes, particularly in response to stress. Individuals with schizotypal personality disorder may also experience symptoms of anxiety, depression, and/or transient psychotic episodes.

In certain embodiments, methods provided are drawn to the treatment of the psychiatric illness associated with an eating disorder. In other embodiments, methods provided do not include the treatment of eating disorders. In certain embodiments, methods provided do not include the treatment of anorexia. In other embodiments, methods provided may be used for treating the psychiatric illness associated with anorexic subjects. In certain embodiments, methods provided do not include the treatment of binge eating.

In certain embodiments, methods for treating psychiatric disorders in a subject are provided, wherein the method comprises administering to a subject in need thereof an NMX peptide, an FNX peptide, or an NMX receptor agonist, or an analog or a derivative thereof, in an amount effective to treat the psychiatric disorder. Certain embodiments contemplate the use of the naturally occurring and peripherally secreted NMX peptide, FNX peptide, or an NMX receptor agonist for the treatment of the psychiatric disorder. In some instances, the psychiatric disorders are of natural or unidentified etiology.

In certain embodiments, it is contemplated that compounds that reduce or moderate stress, or regulate the stress pathway, may be useful as pharmacotherapeutic agents. In other embodiments, it is contemplated that compounds that can affect or regulate metabolic disturbances as well as psychiatric or behavioral processes would be useful as pharmacotherapeutic agents. In yet other embodiments, it is contemplated that compounds that can attenuate or reverse metabolic disturbances would be useful as pharmacotherapeutic treatments of psychiatric diseases or disorders. Certain embodiments contemplate the use of compounds that can treat both the psychiatric disease and metabolic disturbances present in a subject. It is contemplated that compounds useful in the methods provided may be NMX peptides, FNX peptides, or NMX receptor agonists, or analogs or derivatives thereof.

Without wishing to be bound by theory, it is believed that medicines that not only treat the psychiatric illness but also alleviate the physical co-morbidities of the illness would be expected to elicit an increased rate of treatment response and outcome success in subjects with a psychiatric disease or disorder. Physical co-morbidities, for example without limitation obesity, exacerbate the morbidity that attends psychiatric disease or disorder and lead to a reduction in treatment response. NMX peptides, FNX peptides, or NMX receptor agonists, or analogs or derivatives thereof, may be particularly useful in the methods described herein because of anti-obesigenic and appetite suppressant effects. These effects may increase the rate of treatment response and outcome success in certain subject populations who suffer a psychiatric disease or disorder and who exhibit obesity, obesity-related disease, or eating disorders, for example without limitation diabetes, metabolic syndrome, obesity, Cushing's syndrome, Cushing's disease, atypical major depression, schizophrenia, seasonal affective disorder, polycystic ovary syndrome, post-traumatic stress disorder, night eating syndrome, bulimia nervosa, binge eating disorder, and chronic fatigue syndrome. In certain embodiments, the methods do not include treatment of anorexia. In other embodiments, the methods include treating the psychiatric illness associated with anorexia.

NMX peptides, FNX peptides, or NMX receptor agonists, or analogs or derivatives thereof, may be superior to some other anxiolytic and/or antipsychotic agents, for example, as certain compounds contemplated herein do not promote weight gain and, in fact, may induce weight loss. This attribute of NMX peptides, FNX peptides, or NMX receptor agonists or analogs or derivatives thereof, may lead to greater compliance among subjects being treated for psychiatric disease or disorder. Central administration of NMU to rats and peripheral (intraperitoneal) administration of NMX and FNX peptides to mice inhibited food intake by the animals. See, for example, Wren et al., 2002, *Endocrinology* 143:4227-4234 and commonly-owned PCT Patent Application No. PCT/US2006/047953 (WO 2007/075439), incorporated herein by reference in its entirety and for all purposes.

It is further contemplated that an NMX peptide, an FNX peptide, or an NMX receptor agonist, or an analog or a derivative thereof, may be used in conjunction with at least one other medication or therapy for treating a psychiatric disease or disorder, including, but not limited to, those conventionally used to treat psychiatric disease, such as tricyclic antidepressants and the monoamine oxidase inhibitors (MAOIs), selective serotonin reuptake inhibitors (SSRIs), serotonin and noradrenaline reuptake inhibitors (SNRIs), herbal antidepressants (e.g., St John's Wort or Hypericum), SGAs, psychoanalysis, cognitive-behavioral therapy, and interpersonal therapy.

Second generation antipsychotics (SGAs) (also known as "atypical antipsychotics") are a class of medication with a broad spectrum of neurotransmitter activity, having affinity for not only the dopamine $D_2$, but also $D_1$, $D_3$, and $D_4$ receptors, as well as for serotonin, adrenergic, histamine, and/or opiate receptors. SGAs can be well tolerated, having fewer and less severe side effects compared with other antipsychotics, and with few to no extrapyramidal side effects at clinical doses. Many of these newer medications are also more effective at treating the negative, cognitive, and affective symptoms. Thus, SGAs are now considered the first-line interventions for psychotic disorders. One of the atypical agents, clozapine, is clearly the most effective antipsychotic, but clozapine is reserved as a second-line agent, indicated only after other medications have failed or in patients at high risk for suicidal behavior, because it can cause agranulocytosis (American Diabetes Association, American Psychiatric Association, American Association of Clinical Endocrinologists, North American Association for the Study of Obesity, *J. Clin. Psychiatry.*, 2004, 65 (2):267-72; Leo, et al., 2000, *Prim. Care Companion J. Clin. Psychiatry* 2 (6):194-204). SGAs are widely prescribed, to approximately 3 percent of the U.S. population, for treatment of schizophrenia, bipolar disorder, depression and dementia. However, concern has arisen regarding weight gain, obesity and an increased risk of diabetes associated with the use of SGAs (Ader, et al., 2005, *Diabetes* 54:862-871).

In some embodiments, the NMX, FNX, or NMX receptor agonist, or analog or derivative thereof, may be used in conjunction with an amylin or its agonists, analogs, or derivatives, as the at least one other medication for treating a psychiatric disease or disorder. Examples of amylin, amylin agonists, amylin analogs, and derivatives thereof, for such a use include those described in U.S. Pat. Nos. 5,686,411, 6,610,824, 5,998,367, 6,087,334, 6,114,304, 6,410,511; and PCT Application Publication Nos. WO 93/10146, WO 2006/042242, WO 2006/083254, and WO 2006/105527, all of which are incorporated herein by reference in their entireties and for all purposes. In certain embodiments, use of amylin agonists may not include the use of calcitonins. In certain embodiments, the calcitonin is salmon calcitonin. In other embodiments, use of amylin agonists may not include the use of CGRP. In still other embodiments, use of amylin agonists may not include the use of analogs of CGRP or calcitonin. Accordingly, it is contemplated that use of amylin agonists provided may include a proviso that excludes CGRP, calcitonin, or analogs thereof. In some embodiments, the at least one other psychiatric medication is not an amylin, an amylin agonist, an amylin analog, or an amylin derivative.

When used in conjunction with other medications or therapies for treating a psychiatric disease or disorder, administration of the NMX peptide, FNX peptide, or NMX receptor agonist, or analog or derivative thereof, may occur concurrently or sequentially with the other medication(s), therapy or therapies. For example, the NMX peptide, FNX peptide, or NMX receptor agonist, or analog or derivative thereof, may be administered during the same time period as the other psychiatric medication, during an overlapping time period as the other psychiatric medication, or in a time period that does not overlap with administration of the other psychiatric medication. As a combination or add-on therapy, the beneficial qualities of an NMX peptide, an FNX peptide, or an NMX receptor agonist, or an analog or a derivative thereof, may counteract or moderate one or more unwanted side effects of currently available medications, for example without limitation anxiety, weight gain, diabetes, and the like.

For example, SGAs are effective therapeutics for the treatment of symptoms associated with schizophrenia and related psychotic conditions. Despite advances in treating the psychiatric condition afforded by SGAs, accumulating clinical data have revealed an association between the use of SGAs and weight gain, diabetes, and dyslipidemia (American Diabetes Association et al., 2004, *Diabetes Care* 27:596-601). Weight gain may be one contributing factor to non-compliance of a subject with a medication regimen. So, as good as any medication may be, it does not provide any benefit to a subject that is not taking it, or not taking it properly. Exemplary SGAs such as clozapine and olanzapine have been identified as being likely to produce weight gain. Additionally, these two SGAs have also been associated with increased risk for both diabetes and dyslipidemia. The ability of an NMX peptide, an FNX peptide, or an NMX receptor agonist, or an analog or a derivative thereof, to effectively reduce body weight gain induced by clozapine treatment is of use to the recipient. Accordingly, an NMX peptide, an FNX peptide, or an NMX receptor agonist, or an analog or a derivatives thereof, is also able to treat or aid in the treatment of diabetes and dyslipidemia. Accordingly, when used with other psychiatric medications, an NMX peptide, an FNX peptide, or an NMX receptor agonist, or an analog or a derivative thereof, may not only provide an additional treatment to the psychiatric condition but also be able to counteract at least a negative side effect of those other psychiatric medications.

An NMX peptide, an FNX peptide, or an NMX receptor agonist, or an analog or a derivative thereof may have anxiolytic and/or antipsychotic activities that are not directed related an anti-obesity activity of the compound.

As used herein, a "subject" may include any mammal, including humans. A "subject" may also include pets and commercial animals (e.g., dogs, cats, horses), as well as other animals. Subjects may have at least one of the psychiatric disorders described herein. Subjects who may benefit from the methods disclosed herein may be overweight or obese; however, they may also be lean. They may have a metabolic disorder or condition in addition to a psychiatric disorder. Exemplary metabolic disorders include diabetes, metabolic syndrome, insulin-resistance, and dyslipidemia. Subjects can be of any age. Accordingly, these disorders can be found in young adults and adults (defined herein as those aged 65 or under) as well as infants, children, adolescents, and the elderly (defined herein as over the age of 65).

As used herein, and as well-understood in the art, "treatment" is an approach for obtaining beneficial or desired results, including clinical results. "Treating" or "palliating" a disease, disorder, or condition means that the extent, undesirable clinical manifestations of a condition, or both, of a disorder or a disease state are lessened and/or time course of the progression is slowed or lengthened, as compared to not treating the disorder. For purposes of the methods disclosed herein, beneficial or desired clinical results include, but are not limited to, alleviation or amelioration of one or more symptoms, diminishment of extent of disorder, stabilized (i.e., not worsening) state of disorder, delay or slowing of disorder progression, amelioration or palliation of the disorder, and remission (whether partial or total), whether detectable or undetectable. "Treatment" can also mean prolonging survival as compared to expected survival if not receiving treatment. Further, treating does not necessarily occur by administration of one dose, but often occurs upon administration of a series of doses. Thus, a therapeutically effective amount, an amount sufficient to palliate, or an amount sufficient to treat a disease, disorder, or condition may be administered in one or more administrations.

As used herein, the term "therapeutically effective amount" means an amount of active compound in the composition that will elicit a biological response that is sought in a cell, tissue, system, and/or subject (including a human being), which includes without limitation, alleviation and/or prevention of the symptom(s) of a disorder or condition being treated and/or prevented. As used herein, the term "symptom(s)" refers to any marker(s) of the condition, disease or disorder (collectively referred to herein as a "condition" unless context dictates otherwise) which can be observed directly or indirectly and can include, but is not limited to, physiological response(s) and/or the expression of particular biomarker(s) (e.g., protein(s), peptide(s), nucleic acid(s), metabolites, molecule(s), etc.) associated with a disorder or condition, and/or the progression of a disorder or condition.

As used herein, the terms "protein", "polypeptide" or "peptide" include any molecule that comprises five or more amino acids. It is well known in the art that proteins may undergo modification, including post-translational modifications such as, but not limited to, disulfide bond formation, glycosylation, phosphorylation, or oligomerization. Thus, as used herein, the term "protein" or "peptide" includes any protein or peptide that is modified by any biological or non-biological process. In certain contexts, as used herein, a "peptide" refers to a polymer comprising less than about 200 amino acid residues, less than about 100 amino acid residues, less than about 50 amino acid residues, or less than about 40 amino acids. Generally, "peptides" as used herein do not include polyamino acids unless explicitly referred to as such. Also, generally, unless context dictates otherwise, as used herein the term "peptide", "polypeptide" and "protein" are used herein interchangeably.

As used herein, the singular form "a", "an", and "the" includes plural references unless otherwise indicated or clear from context. For example, as will be apparent from context, "an" FNX peptide can include one or more FNX peptides. The term "about" in the context of a numeric value can refer to the numerical value +/−10% thereof.

"NMX peptide" refers to a neuromedin U (NMU), a neuromedin S (NMS), or an FN-38 peptide, including FNX peptides as described herein. The polypeptide may be obtained or derived from any species. Thus, the term includes the human full-length amino acid peptides, and species variations thereof, including for example without limitation murine, hamster, chicken, bovine, rat, and dog polypeptides. In this sense the descriptors "wild-type," "native" and "unmodified" are used interchangeably.

By "NMX Receptor agonist" is meant any compound, including peptide, peptide-like compounds and small molecules, that elicits similar biological activities as FN-38 and acts on a known NMU or NMS receptor, e.g., NMUR1 or NMUR2.

FNX peptides for use in the methods provided herein include those described in commonly-owned PCT Patent Application No. PCT/US2006/047953 (WO 2007/075439), which is incorporated herein by reference in its entirety and for all purposes. In particular, the NMX and FNX peptides described in WO 2007/075439 are incorporated herein by reference and for all purposes.

Exemplary NMX peptides include, but are not limited to, the peptides provided in Table 1.

TABLE 1

Exemplary NMX peptides

| SEQ ID NO: | Description | Sequence |
|---|---|---|
| 1 | human NMU | FLFHYSKTQKLGKSNVVEEFQSPFAS QSRGYFLFRPRNGRRSAGF |
| 2 | rat NMU variant CAD52851 | FLFHYSKTQKLGNSNVVEYQGPVAPS GGFFLFRPRN |
| 3 | tree frog NMU variant CAD52850 | FLFHYSKSHDSGNSDITEEVQVPGGV ISNGYFLFRPRN |
| 4 | chicken NMU variant | FLFHYSKTHDSGNSDVREDLQGTGGI QSRGYFFFRPRN |
| 5 | human FN-38 | FLFHYSKTQKLGKSNVVEELQSPFAS QSRGYFLFRPRN |
| 6 | FN-38(1-28) | FLFHYSKTQKLGKSNVVEELQSPFAS QS |
| 7 | FN-38(1-15) | FLFHYSKTQKLGKSN |
| 8 | human NMS | ILQRGSGTAAVDFTKKDHTATWGRPF FLFRPRN |
| 9 | rat NMS | LPRLLHTDSRMATIDFPKKDPTTSLG RPFFLFRPRN |

Additional examples of NMX peptides include, but are not limited to, the peptides provided in Table 2.

TABLE 2

Additional exemplary NMX peptides

| SEQ ID NO: | Description | Sequence |
|---|---|---|
| 10 | porcine NMU U8 (octapeptide) | YFLFRPRN |
| 11 | rat NMU-23 | YKVNEYQGPVAPSGGFFLFRPRN |
| 12 | human NMU U9 | GYFLFRPRN |
| 13 | tree frog SN-23 | SDEEVQVPGGVISNGYFLFRPRN |

Other exemplary peptides include the peptides provided in Table 3.

TABLE 3

Other exemplary peptides

| SEQ ID NO: | Description | Sequence |
|---|---|---|
| 14 | FN-38(1-15)-SN-23 | FLFHYSKTQKLGKSNSDE EVQVPGGVISNGYFLFRPRN |
| 15 | FN-38(1-15)-SN-23 (des-octapeptide) | FLFHYSKTQKLGKSNSDEE VQVPGGVISNG |
| 16 | FN-38(des-octapeptide) | FLFHYSKTQKLGKSNVVEELQ SPFASQSRG |
| 17 | human NMU25 | FRVDEEFQSPFASQSRGYFL FRPRN |

FN-38(1-15)-SN-23 (SEQ ID NO:14) is a hybrid of tree frog SN-23 NMU (tree frog SN-23 (SEQ ID NO:13) and human FN-38(1-15) (SEQ ID NO:7).

NMX peptides, FNX peptides, and NMX receptor agonists, and analogs and derivatives thereof which are peptides may or may not be amidated at the C-terminal end. The term "des-octapeptide" in the context of a peptide described herein refers to deletion of the residues forming the C-terminal octapeptide.

As used herein, the names of some compounds indicate both the peptide upon which the compound is based (e.g., the base peptide) and the modification(s) made to the base peptide sequence. "Base peptide," "base reference peptide," "reference peptide" and like terms refer to a peptide which serves as a basis for analogous peptides having, for example, insertions, substitutions, extensions, and/or deletions of the amino acid sequence of the base peptide, as known in the art. For example, "FN-38(1-15)," "FN-38$_{1-15}$" and the like refer to a peptide based on the sequence of amino acids 1-15 of FN-38. An amino acid preceded by a superscript number indicates that the amino acid so indicated replaces the amino acid normally present at the amino acid position of the superscript in the base peptide sequence. For example, "FN-38-$^{31}$F," "FN-38-($^{31}$F)" and "[$^{31}$F]-FN-38" and the like refer to a peptide based on the sequence of FN-38 having Phe at residue 31. The term "des-" preceding one or more amino acids indicates that the named amino acids normally present at the positions of the superscripts in the base peptide sequence are deleted. For example, "FN-38 des-($^{24}$F-$^{27}$Q)" and "des-($^{24}$F-$^{27}$Q)-FN-38" refer to a peptide based on the sequence of FN-38 having amino acids Phe through Gln at positions 24 through 27 deleted.

In some embodiments, FNX peptides comprise an amino acid sequence of Formula I (F1-P) or Formula II (F2-P), as described in PCT Patent Application No. PCT/US2006/047953 (WO 2007/075439), incorporated herein by reference in its entirety and for all purposes.

In Formula I peptides, the F1 portion is a des-octapeptide portion of FN-38 or analog, derivative or chimera thereof. An exemplary F1 portion is (SEQ ID NO: 16)
FLFHYSKTQKLGKSNVVEELQSPFASQSRG.

In Formula II peptides, the F2 portion is a des-octapeptide portion of FN-38 or SN-23, or hybrid, analog, derivative or chimera thereof. An exemplary F2 portion is (SEQ ID NO: 15)
FLFHYSKTQKLGKSNSDEEVQVPGGVISNG.

Exemplary octapeptide sequences ("P") for use in peptides comprising Formula I or Formula II include, but are not limited to, those provided in Table 4.

TABLE 4

Exemplary octapeptide sequences ("P")

| SEQ ID NO: | Sequence |
|---|---|
| 18 | YFLFRPRN |
| 19 | YFLYRPRN |
| 20 | YFVFRPRN |
| 21 | FFLFRPRN |
| 22 | YFLVRPRN |
| 23 | YFFFRPRN |
| 24 | YFLFHPRN |
| 25 | YFLFRPHN |
| 26 | YFLFR(beta turn mimic B)RN |

Additional examples of octapeptide sequences ("P") with multiple substitutions or modification to increase its hydrophobicity and/or its positive charge include, but are not limited to, the peptides provided in Table 5.

TABLE 5

Additional exemplary octapeptide sequences ("P")

| SEQ ID NO: | Sequence |
|---|---|
| 27 | FFFYHPHN |
| 28 | FFFFRPRN |
| 29 | FFFFKHHN |
| 30 | FFFFK(beta turn mimic B)HN |

In certain embodiments, FNX peptides have one of the octapeptide sequences ("P"). In some embodiments, FNX peptides have two, three, four, five, or six of the octapeptide substitutions or modifications shown herein. In some embodiments, a P region octapeptide does not have a histidine substituting for either or both arginine residues. In some embodiments, a P region octapeptide does not have a turn mimic substituting for proline. Exemplary analogs of FNX peptide FN-38 (SEQ ID NO:5) having a P region sequence as described herein and an F1 region of FN-38 include without limitation the peptides provided in Table 6.

TABLE 6

Exemplary analogs of FNX peptide FN-38

| SEQ ID NO: | Description | Sequence |
|---|---|---|
| 31 | FN-38-($^{31}$F) | FLFHYSKTQKLGKSNVVEELQSPFASQSRGFFLFRPRN |
| 32 | FN-38-($^{34}$V) | FLFHYSKTQKLGKSNVVEELQSPFASQSRGYFLVRPPN |
| 33 | FN-38-($^{33}$F) | FLFHYSKTQKLGKSNVVEELQSPFASQSRGYFFFRPRN |
| 34 | FN-38-($^{35}$H) | FLFHYSKTQKLGKSNVVEELQSPFASQSRGYFLFHPRN |
| 35 | FN-38-($^{37}$H) | FLFHYSKTQKLGKSNVVEELQSPFASQSRGYFLFRPHN |
| 36 | FN-38-$^{36}$(beta turn mimic B) | FLFHYSKTQKLGKSNVVEELQSPFASQSRGYFLFR(beta turn mimic B)RN |
| 37 | FN-38-($^{31}$F $^{33}$F $^{34}$Y $^{35}$H $^{37}$H) | FLFHYSKTQKLGKSNVVEELQSPFASQSRGFFFYHPHN |
| 38 | FN-38-($^{31,33}$F) | FLFHYSKTQKLGKSNVVEELQSPFASQSRGFFFFRPRN |
| 39 | FN-38-($^{31}$F $^{33}$F $^{35}$K $^{36}$H $^{37}$H) | FLFHYSKTQKLGKSNVVEELQSPFASQSRGFFFFKHHN |
| 40 | FN-38 ($^{31}$F $^{33}$F $^{35}$K $^{36}$(beta turn mimic B) $^{37}$H) | FLFHYSKTQKLGKSNVVEELQSPFASQSRGFFFFK(beta turn mimic B)HN |

Exemplary analogs of Formula II having a P sequence and the F2 region of FN-38(1-15)-SN-23 (SEQ ID NO:14) include, but are not limited to the peptides provided in Table 7.

TABLE 7

Exemplary analogs of Formula II

| SEQ ID NO: | Description | Sequence |
|---|---|---|
| 41 | FN-38(1-15)-SN-23-$^{31}$F | FLFHYSKTQKLGKSNSDEEVQVPGGVISNGFFLFRPRN |
| 42 | FN-38(1-15)-SN-23-$^{34}$V | FLFHYSKTQKLGKSNSDEEVQVPGGVISNGYFLVRPRN |
| 43 | FN-38(1-15)-SN-23-$^{33}$F | FLFHYSKTQKLGKSNSDEEVQVPGGVISNGYFFFRPRN |
| 44 | FN-38(1-15)-SN-23-$^{35}$H | FLFHYSKTQKLGKSNSDEEVQVPGGVISNGYFLFHPRN |
| 45 | FN-38(1-15)-SN-23-$^{37}$H | FLFHYSKTQKLGKSNSDEEVQVPGGVISNGYFLFRPHN |
| 46 | FN-38(1-15)-SN-23-$^{36}$(beta turn mimic B) | FLFHYSKTQKLGKSNSDEEVQVPGGVISNGYFLFR(beta turn mimic B)RN |
| 47 | FN-38(1-15)-SN-23-$^{31}$F$^{33}$F$^{34}$Y$^{35}$H$^{37}$H | FLFHYSKTQKLGKSNSDEEVQVPGGVISNGFFFYHPHN |
| 48 | FN-38(1-15)-SN-23-$^{31,33}$F | FLFHYSKTQKLGKSNSDEEVQVPGGVISNGFFFFRPRN |
| 49 | (FN-38(1-15)-SN-23-$^{31,33}$F$^{35}$K$^{36,37}$H | FLFHYSKTQKLGKSNSDEEVQVPGGVISNGFFFFKHHN |
| 50 | (FN-38(1-15)-SN-23-$^{31,33}$F$^{35}$K$^{36}$(beta turn mimic B)$^{37}$H | FLFHYSKTQKLGKSNSDEEVQVPGGVISNGFFFFK(beta turn mimic B)HN |

In certain embodiments, FNX peptides for use in the methods provided herein have one or more amino acid deletions or deleted regions, for example without limitation, the deletions and deleted regions shown herein. In other embodiments, an FNX peptide has two such deleted regions. In other embodiments, an FNX peptide has at least one amino acid deletion, the amino acid being any one of the amino acids contained within any of the deleted regions shown below. In other embodiments, one, two, three, four, or five amino acids are deleted. Accordingly, depending on the length of the parent peptide, the FNX peptide may be at least or equal to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, or 43 residues in length or any combination thereof, e.g., at least 10 but no more than 15 residues. In certain embodiments, the deleted amino acids are of the amino acids contained in any of the deleted regions shown herein.

Exemplary FNX peptides with amino acids deletions include, but are not limited to, the deletion and/or substitution analogs of FN-38 (SEQ ID NO:5) and FN-38(1-15)-SN-23 (SEQ ID NO:14) provided in Table 8, wherein dashes indicate locations of deleted amino acid residues.

TABLE 8

Exemplary FNX peptides with amino acids deletions

| SEQ ID NO: | Description | Sequence |
|---|---|---|
| 51 | FN-38 des-($^{16}$V-$^{17}$V) | FLFHYSKTQKLGKSN--EELQSPFASQSRGYFLFRPRN |
| 52 | FN-38 des-($^{24}$F-$^{27}$Q) | FLFHYSKTQKLGKSNVVEELQSP----SRGYFLFRPRN |
| 53 | FN-38 des-($^{16}$V-$^{17}$V, $^{24}$F-$^{27}$Q) | FLFHYSKTQKLGKSN--EELQSP----SRGYFLFRPRN |
| 54 | FN-38 des ($^{1}$F-$^{4}$H) | ----YSKTQKLGKSNVVEELQSPFASQSRGYFLFRPRN |
| 55 | FN-38 des-($^{6}$S-$^{9}$Q) | FLFHY----KLGKSNVVEELQSPFASQSRGYFLFRPRN |
| 56 | FN-38 des-($^{13}$K-$^{19}$E) | FLFHYSKTQKLG-------LQSPFASQSRGYFLFRPRN |
| 57 | FN-38 des-($^{2}$L-$^{8}$T) | F-------QKLGKSNVVEELQSPFASQSRGYFLFRPRN |

TABLE 8-continued

Exemplary FNX peptides with amino acids deletions

| SEQ ID NO: | Description | Sequence |
|---|---|---|
| 58 | FN-38 des-($^7$K-$^{23}$P) | FLFHYS----------------FASQSRGYFLFRPRN |
| 59 | FN-38 des-($^{16}$V-$^{29}$R) | FLFHYSKTQKLGKSN-------------GYFLFRPRN |
| 60 | FN-38 des-($^{16}$V-$^{27}$Q) | FLFHYSKTQKLGKSN-----------SRGYFLFRPRN |
| 61 | FN-38 des-($^{16}$V-$^{17}$V, $^{24}$F-$^{27}$Q) $^{35}$K | FLFHYSKTQKLGKSN--EELQSP----SRGYFLFKPRN |
| 62 | FN-38 des-($^7$K-$^{29}$R) | FLFHYS--------------------GYFLFRPRN |
| 63 | FN-38 des-($^1$F-$^9$Q) | ---------KLGKSNVVEELQSPFASQSRGYFLFRPRN |
| 64 | FN-38 des-($^1$F-$^4$H, $^{16}$V-$^{17}$V, $^{24}$F-$^{27}$Q) | ----YSKTQKLGKSN--EELQSP----SRGYFLFRPRN |
| 65 | FN-38 des-($^7$K-$^{29}$R) $^{36}$(beta turn mimic B) | FLFHYS--------------------GYFLFR (beta turn mimic B) RN |
| 66 | FN-38 des-($^7$K-$^{29}$R), $^{31}$F, $^{36}$(beta turn mimic B) $^{37}$H | FLFHYS--------------------GFFLFR(beta turn mimic B)HN |
| 67 | FN-38 des-($^7$K-$^{29}$R), $^{35}$K | FLFHYS--------------------GYFLFKPRN |
| 68 | FN-38 des-($^7$K-$^{29}$R), $^{31}$F | FLFHYS--------------------GFFLFRPRN |
| 69 | FN-38 des-($^7$K-$^{29}$R), $^{31}$F, $^{35}$K | FLFHYS--------------------GFFLFKPRN |
| 70 | FN-38(1-15)-SN-23 des-($^{16}$S-$^{17}$D)) | FLFHYSKTQKLGKSN--EEVQVPGGVISNGYFLFRPRN |
| 71 | FN-38(1-15)-SN-23 des-($^{24}$G-$^{27}$I)) | FLFHYSKTQKLGKSNSDEEVQVP----SNGYFLFRPRN |
| 72 | FN-38(1-15)-SN-23 des-($^{16}$S-$^{17}$D, $^{24}$G-$^{27}$I) | FLFHYSKTQKLGKSN--EEVQVP----SNGYFLFRPRN |
| 73 | FN-38(1-15)-SN-23 des-($^1$F-$^4$H) | ----YSKTQKLGKSNVVEELQSPFASQSRGYFLFRPRN |
| 74 | FN-38(1-15)-SN-23 des-($^6$S-$^9$Q) | FLFHY----KLGKSNVVEELQSPFASQSRGYFLFRPRN |
| 75 | FN-38(1-15)-SN-23 des-($^{13}$K-$^{19}$E) | FLFHYSKTQKLG-------VQVPGGVISNGYFLFRPRN |
| 76 | FN-38(1-15)-SN-23 des-($^2$L-$^8$T) | F-------QKLGKSNSDEEVQVPGGVISNGYFLFRPRN |

NMX peptides, FNX peptides, and NMX receptor agonists, and analogs or derivatives thereof, that contain modified peptide character are included within the methods provided. Such peptide mimetics may include, for example, one or more of the following substitutions for —CO—NH— amide bonds: depsipeptides (—CO—O—), iminomethylenes (—CH$_2$—NH—), trans-alkenes (—CH═CH—), beta-enaminonitriles (—C(═CH—CN)—NH—), thioamides (—C(S)—NH—), thiomethylenes (e.g., —S—CH$_2$—, —CH$_2$—S—), methylenes (—CH$_2$—), alkylenes (e.g., —(CH$_2$)$_n$—, n>1) and retro-amides (—NH—CO—).

By "agonist" is meant a compound which elicits a biological activity of a reference peptide. In certain aspects, an agonist has a greater potency than the reference peptide, or within five orders of magnitude (plus or minus) of potency compared to the reference peptide, for example 4, 3, 2, or 1 order of magnitude, when evaluated by art-known measures such as, for example, receptor activation studies, ligand binding/competition studies, receptor binding/competition studies. In one aspect, an agonist will bind in such assays with an affinity of greater than about 1 µM, and in certain aspects, with an affinity of greater than about 1-5 nM. An agonist can be a fragment of a reference peptide which retains potency or displays enhanced potency compared to the reference peptide and/or can be an analog of the reference peptide. In one aspect, an agonist can modulate the therapeutic efficacy, scope, duration of action, physicochemical properties, and/or other pharmacokinetic properties of a bioactive peptide or receptor molecule.

As used herein, "analog" refers to a peptide which sequence is derived from that of the base reference peptide, e.g., NMU, FN-38, etc., and includes insertions, substitutions, extensions, and/or deletions of the reference amino acid sequence, for example having at least 50% or 55% amino acid sequence identity with the base reference peptide. In certain embodiments, an analog may have at least 50%, 55%, 60%, 65%, 70%, 75%, 80%, 82%, 84%, 86%, 88%, 90%, 92%, 94%, 95%, 96%, 97%, 98% or even 99% amino acid sequence identity with the base reference peptide. In one embodiment, such analogs may comprise conservative or non-conservative amino acid substitutions (including non-natural amino acids and L and D forms). A "conversative" amino acid substitution maintains charge, hydrophobicity and/or other amino acid property. Exemplary conservative substitutions include without limitation Ile for Leu, Arg for Lys, Tyr for Phe, and the like as well known in the art. Analogs include compounds having agonist and compounds having antagonist activity. As used herein "analog" further refers to bioactive peptides or proteins that are structurally related to a parent peptide by amino acid sequence but which may differ from the parent in a characteristic of interest such as for example without limitation bioactivity, solubility, resistance to proteolysis, and the like. In certain embodiments, analogs have activities between about 1% to about 10,000%, about 10% to about 1000%, and about 50% to about 500% of the bioactivity of the parental peptide.

As contemplated herein, NMX analogs may be compounds having at least 50%, 55%, 60%, 65%, 70%, 75%, 80%, 82%, 84%, 86%, 88%, 90%, 92%, 94%, 95%, 96%, 97%, 98% or even 99% amino acid sequence identity to any NMX peptide amino acid sequence described herein. In some embodiments, NMX analogs may also be compounds having at least 50%, 55%, 60%, 65%, 70%, 75%, 80%, 82%, 84%, 86%, 88%, 90%, 92%, 94%, 95%, 96%, 97%, 98% or even 99% amino acid sequence identity to any NMX peptide amino acid sequence described herein and having NMX activity. In some embodiments, an NMX analog may be a compound having at least 50%, 55%, 60%, 65%, 70%, 75%, 80%, 82%, 84%, 86%, 88%, 90%, 92%, 94%, 95%, 96%, 97%, 98% or even 99% amino acid sequence identity to human NMU and having NMX activity.

In certain embodiments, FNX analogs may be compounds having at least 50%, 55%, 60%, 65%, 70%, 75%, 80%, 82%, 84%, 86%, 88%, 90%, 92%, 94%, 95%, 96%, 97%, 98% or even 99% amino acid sequence identity to any of the FNX peptide amino acid sequence described herein. In some embodiments, FNX analogs contemplated herein may also be compounds having at least 50%, 55%, 60%, 65%, 70%, 75%, 80%, 82%, 84%, 86%, 88%, 90%, 92%, 94%, 95%, 96%, 97%, 98% or even 99% amino acid sequence identity to any of the FNX peptide amino acid sequence described herein and having FNX activity. In some embodiments, an FNX analog may be a compounds having at least 50%, 55%, 60%, 65%, 70%, 75%, 80%, 82%, 84%, 86%, 88%, 90%, 92%, 94%, 95%, 96%, 97%, 98% or even 99% amino acid sequence identity to the FN-38 (SEQ ID NO:5) amino acid sequence and having FNX activity. In other embodiments, an FNX analog may be a compound having at least 50%, 55%, 60%, 65%, 70%, 75%, 80%, 82%, 84%, 86%, 88%, 90%, 92%, 94%, 95%, 96%, 97%, 98% or even 99% amino acid sequence identity to FN-38(1-15)-SN-23 amino acid sequence (SEQ ID NO:14) and having FNX activity.

In certain embodiments, NMX analogs include those with insertions, deletions, extensions, truncations, and/or substitutions in at least one or more amino acid positions of any of the NMX peptides or analogs described herein. FNX analogs also include those with insertions, deletions, extensions, truncations, and/or substitutions in at least one or more amino acid positions of any of the FNX peptides or analogs described herein. The number of amino acid insertions, deletions, or substitutions may be at least 1, 2, 3, 4, 5, 10, 15, 20 or even 25 amino acid insertions, deletions, or substitutions. In certain embodiments, the number of amino acid insertions, deletions, or substitutions may be not more than 1, 2, 3, 4, 5, 10, 15, 20, 25 or even 30 amino acid insertions, deletions, or substitutions. Insertions, extensions, or substitutions may be with other natural amino acids, synthetic amino acids, peptidomimetics, or other chemical compounds.

"Derivative" refers to a molecule having the amino acid sequence of a native or parent NMX, FNX, NMX receptor agonist, or analog thereof, and additionally having a chemical modification of one or more amino acid side groups, α-carbon atoms, terminal amino group, or terminal carboxylic acid group. Contemplated chemical modification includes, but is not limited to, adding chemical moieties, creating new bonds, and removing chemical moieties. The peptides may be derivatized by chemical alterations such as amidation, glycosylation, acylation, sulfation, phosphorylation, acetylation, and cyclization. Such chemical alterations may be obtained through chemical or biochemical methodologies, as well as through in vivo processes, or any combination thereof. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino group include without limitation, the desamino, N-lower alkyl, N-di-lower alkyl, constrained alkyls (e.g. branched, cyclic, fused, adamantyl) and N-acyl modifications as known in the art. Modifications of the terminal carboxy group include without limitation, the amide, lower alkyl amide, constrained alkyls (e.g. branched, cyclic, fused, adamantyl,) alkyl, dialkyl amide, and lower alkyl ester modifications. Lower alkyl is $C_1$-$C_4$ alkyl. Furthermore, one or more side groups, or terminal groups, may be protected by protective groups known to the ordinarily-skilled synthetic chemist. The α-carbon of an amino acid may be mono- or dimethylated. NMX and FNX peptides, and analogs and derivatives thereof include acid as well as amide forms of the peptides.

Derivatives of the peptides and analogs are also included within the methods provided in which the stereochemistry of individual amino acids may be inverted from (L)/S to (D)/R at one or more specific sites. Also included within the methods provided are the peptides and analogs modified by glycosylation of Asn, Ser and/or Thr residues. Compounds useful in the methods provided may also be biologically active fragments of the peptides (native, agonist, analog, and derivative) herein described.

Derivatives of the peptides and analogs described herein may also include conjugation to one or more polymers or small molecule substituents. One type of polymer conjugation is linkage or attachment of polyethylene glycol (PEG) polymers, polyamino acids (e.g., poly-his, poly-arg, poly-lys, etc.) and/or fatty acid chains of various lengths to the N- or C-terminus or amino acid residue side chains of an NMX or FNX peptide. Small molecule substituents include lower alkyls, alkyls and constrained alkyls (e.g., branched, cyclic, fused, adamantyl), and aromatic groups. In addition, basic residues such as R and K may be replaced with homoR and homoK, citrulline, or ornithine to improve metabolic stability of the peptide.

Compounds useful in the methods provided may further include additional amino acids, chemicals, or moieties that do not affect the biological activity or function of the peptide but may perform other functions, such as aiding purification (e.g., histidine tag), detection (e.g., biotin), increasing solubility or half-life (e.g., pegylation) or expression (e.g., secretion signal peptide).

By "amino acid," "amino acid residue" and like terms are meant natural amino acids, unnatural amino acids, and modified amino acid, all in their D and L stereoisomers if their structure allows such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tert-butylglycine, 2,4-diaminoisobutyric acid, desmosine, 2,2'-diaminopimelic acid, 2,3-diaminopropionic acid, N-ethylglycine, N-ethylasparagine, homolysine, homoproline, homoserine, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline, homolysine, homoarginine, homoserine, citrulline, ornithine, $N_\epsilon$-formyllysine. Modified amino acids include the natural and unnatural amino acids which are chemically blocked, reversibly or irreversibly, or modified on the N-terminal amino group or their side chain groups, for example without limitation, methionine sulfoxide, methionine sulfone, S (carbo) amino group or side chain functional group which has been chemically codified to another functional group. For example, aspartic acid-(beta-methyl ester) is a modified amino acid of aspartic acid; N-ethylglycine is a modified amino acid of glycine; or alanine carboxamide is a modified amino acid of alanine. Additional residues that can be incorporated are described, for example without limitation, in Sandberg et al., 1998, *J. Med. Chem.* 41:2481-2491.

In certain embodiments, the NMX peptide, FNX peptide, NMX receptor agonist, or analog or derivative thereof contemplated herein may include substitutions of one or more unnatural and/or non-amino acids, e.g., amino acid mimetics. In certain embodiments, the non-amino acids are turn mimetics or linker moieties. Exemplary linker moieties include without limitation —NH—X—CO—, wherein X=$(CH_2)_n$ (wherein n can be 2-20), —NH—$CH_2CH_2$—(O—$CH_2CH_2$—O—)$_m$—$CH_2$—CO— (wherein m=1-5,) and other linker moieties known in the art. Preferred linker molecules include aminocaproyl ("Aca"), β-alanyl, and 8-amino-3,6-dioxaoctanoyl. In certain embodiments, turn mimetics contemplated herein are β-turn mimetics as known in the art. Certain β-turn mimetics are available commercially (e.g., BioQuadrant Inc, Quebec, Canada) and have been described in the literature. See Gu et al., 2003, *Tetrahedron Letters* 44: 5863-6; Bourguet et al., 2003, *Bioorganic & Medicinal Chemistry Letters* 13: 1561-4; Grieco et al., 2002, *Tetrahedron Letters* 43: 6297-9; Souers et al., 2001, *Tetrahedron* 57: 7431-48; Tsai et al., 1999, *Bioorganic & Medicinal Chemistry* 7: 29-38; Virgilio et al., 1997, *Tetrahedron* 53: 6635-44. Preferred β-turn mimetics include beta turn mimic A (N-(3S, 6S,9S)-2-oxo-3-amino-1-azabicyclo[4.3.0]-nonane-9-carboxylic acid) and beta turn mimic B (N-(3S,6S,9R)-2-oxo-3-amino-7-thia-1-azabicyclo[4.3.0]-nonane-9-carboxylic acid) illustrated herein.

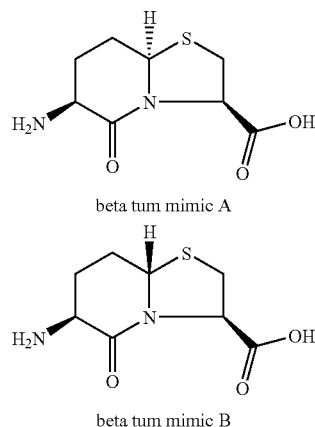

beta turn mimic A beta turn mimic B

"Sequence identity," as is well understood in the art, is a relationship between two or more polypeptide sequences or two or more polynucleotide sequences, as determined by comparing the sequences. In the art, "identity" can also refer to the degree of sequence relatedness between polypeptide or polynucleotide sequences, as determined by the match between strings of such sequences. Identity can be readily calculated by known methods including, but not limited to, those described in *Computational Molecular Biology*, Lesk, ed., Oxford University Press, New York (1988); *Biocomputing: Informatics and Genome Projects*, Smith, ed., Academic Press, New York, 1993; *Computer Analysis of Sequence Data, Part I*, Griffin et al., eds., Humana Press, New Jersey (1994); *Sequence Analysis in Molecular Biology*, von Heinje, Academic Press (1987); *Sequence Analysis Primer*, Gribskov et al., eds., Stockton Press, New York (1991); and Carillo et al., 1988, *SIAM J Applied Math* 48:1073. Methods to determine identity are designed to give the largest match between the sequences tested. Moreover, methods to determine identity are codified in publicly available programs. Computer programs which can be used to determine identity between two sequences include, but are not limited to, GCG (Devereux et al., 1984, *Nucleic Acids Research* 12:387; suite of five BLAST programs, three designed for nucleotide sequences queries (BLASTN, BLASTX, and TBLASTX) and two designed for protein sequence queries (BLASTP and TBLASTN) (Coulson, 1994, *Trends in Biotechnology* 12:76-80; Birren et al., 1997, *Genome Analysis* 1:543-559). The BLASTX program is publicly available from NCBI and other sources (BLAST Manual, Altschul et al., NCBI NLM NIH, Bethesda, Md. 20894; Altschul et al., 1990, *J. Mol. Biol.* 215:403-410). The well known Smith Waterman algorithm can also be used to determine identity. For all percent identity calculations contemplated herein, percent identity is determined by analysis methods and tools well known in the art, for example without limitation the AlignX® module in Vector NTI® (Invitrogen; Carlsbad, Calif.), and the like.

Parameters for polypeptide sequence comparison typically include the following: Algorithm: Needleman & Wunsch, 1970, *J. Mol. Biol.* 48:443-453; Comparison matrix: BLOSUM62 from Hentikoff & Hentikoff, 1992, *Proc. Natl. Acad. Sci. USA* 89:10915-10919; Gap Penalty: 12; Gap Length Penalty: 4. A program that can be used with these parameters is publicly available as the "gap" program from Genetics Computer Group ("GCG"), Madison, Wis. The above parameters along with no penalty for end gap are the default parameters for peptide comparisons. In one embodiment, the BLASTP program of NCBI is used with the default parameters of no compositional adjustment, expect value of 10, word size of 3, BLOSUM62 matrix, gap extension cost of 11, end gap extension cost of 1, dropoff (X) for blast extension (in bits) 7, X dropoff value for gapped alignment (in bits) 15, and final X dropoff value for gapped alignment (in bits) 25.

Parameters for nucleic acid molecule sequence comparison include the following: Algorithm: Needleman & Wunsch, Id.; Comparison matrix: matches—+10; mismatches=0; Gap Penalty: 50; Gap Length Penalty: 3. As used herein, "% identity" is determined using the above parameters as the default parameters for nucleic acid molecule sequence comparisons and the "gap" program from GCG, version 10.2.

As used herein, the term "bioactive" refers to an ability to elicit a biological response that is sought in a cell, tissue, system, and/or subject (including a human being), e.g., a bioactive peptide is one which can be provided in a therapeutically effective amount. For example, in one aspect, a bioactive peptide has biological activity in at least one in vivo hormonal and/or signaling pathway. Biological activity may be evaluated through target receptor binding assays, or through studies that monitor a physiological or behavioral indication, and/or through the measurement of relevant biomarkers, as is known in the art.

In certain embodiments, the FNX peptides can have comparable or higher potency in the treatment and/or prevention of the disease and conditions described herein as compared to native FN-38 polypeptides. In other embodiments, the FNX peptide can have less (e.g., may be 2, 3, 4, or even 5 times less), though still effective, potency in the treatment and/or prevention of the above described conditions, but may possess other desirable characteristics over native FN-38, e.g., increased stability or solubility, less side effects, combination of biological activities, and/or ease in manufacturing, formulating, or use.

Compounds for use in the methods provided form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include, for example, ammonium salts, alkali metal salts (such as sodium and potassium salts) and alkali earth salts (such as calcium and magnesium salts). In certain embodiments, the compounds form acetate, hydrochloride, and trifluoroacetate salts.

"NMX peptide activity," "FNX peptide activity," and "NMX receptor agonist activity" as used herein may include at least one of the activities described herein or known in the art for these compounds. Desirable NMX peptides, FNX peptides, NMX receptor agonists, or analogs or derivatives thereof, may have at least one property shared by the antipsychotic and anxiolytic agents described herein.

Activity as NMX peptides, FNX peptides, NMX receptor agonists, and/or analogs or derivatives thereof, can be confirmed and quantified by performing various screening assays, including receptor (e.g., NMUR1 or NMUR2) binding assays, food intake assays, gastric emptying assays, gastric acid secretion assays, energy expenditure assays, smooth muscle contractility assays, calcium signaling assays in cells expressing NMU receptors, blood pressure assays, heart rate assays, or nociceptive assays. Assays for testing compounds for NMX peptide, an FNX peptide, or NMX receptor agonist activity are known in the art (for example, Brighton et al., 2004, *Pharmacological Rev.* 56:231-248; Westfall et al., 2002, *J. Pharmacol. Exp. Ther.* 301:987-992; Wren et al., 2002, *Endocrinology* 143:4227-4234; Mondal et al., 2003, *Am. J. Physiol. Gastrointest. Liver Physiol.* 284:963-969; Yu et al., 2003, *Neuroscience* 120:467-474; Ida et al., 2005, *Endocrinology* 146:4217-4223; Mori et al., 2005, *EMBO J.* 24:325-335. Exemplary screening methods and assays for testing NMX peptides, FNX peptides, or NMX receptor agonists are also described in PCT Patent Application No. PCT/US2006/047953 (WO 2007/075439), which is incorporated herein by reference in its entirety and for all purposes.

The NMX peptides, FNX peptides, or NMX receptor agonists, or analogs thereof, may be prepared using chemical peptide synthesis techniques known in the art, e.g., using an automated or semi-automated peptide synthesizer, standard recombinant techniques, or both. Derivatives of the NMX peptides, FNX peptides, or NMX receptor agonists, or analogs thereof, may be produced using standard chemical, biochemical, and/or in vivo methodologies as known in the art.

The NMX peptides, FNX peptides, or NMX receptor agonists, or analogs or derivatives thereof, may be synthesized in solution or on a solid support in accordance with conventional techniques. Various automated synthesizers are commercially available and may be used in accordance with known protocols. See, e.g., Stewart et al., 1984, *Solid Phase Peptide Synthesis*, 2d. ed., Pierce Chemical Co.; Tam et al., 1983, *J. Am. Chem. Soc.* 105: 6442; Merrifield, 1986, *Science* 232: 341-347; and Barany et al., 1979, *The Peptides*, Gross et al., eds., Academic Press, NY, 1-284. Solid phase peptide synthesis may be carried out using an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) as examples. For example, solid phase peptide synthesis may be carried out with an automated peptide synthesizer (e.g., Model 430A, Applied Biosystems Inc., Foster City, Calif.) using the NMP/HOBt (Option 1) system and tBoc or Fmoc chemistry with capping (see, *Applied Biosystems User's Manual for the ABI 430A Peptide Synthesizer, Version 1.3, B* Jul. 1, 1988, section 6:49-70). Peptides may also be assembled using an Advanced ChemTech Synthesizer (Model MPS 350, Louisville, Ky.). Peptides may be purified by RP-HPLC (preparative and analytical) using, e.g., a Waters® DELTA-PREPT™ 3000 system (Waters Corp., Milford, Mass.) and a $C_4$, $C_8$, or $C_{18}$ preparative column (10μ, 2.2×25 cm; Grace Vydac, Hesperia, Calif.). The peptide can be readily synthesized and then screened in assays designed to identify peptides with particular activities. Other methods of synthesizing and purifying peptides are known to the skilled artisan.

The NMX peptides, FNX peptides, or NMX receptor agonists, or analogs or derivatives thereof, disclosed herein may alternatively be produced by recombinant techniques well known in the art. See, e.g., Sambrook et al., 1989, *Molecular Cloning: A Laboratory Manual*, 2d ed., Cold Spring Harbor, N.Y. The peptides produced by recombinant technologies may be expressed from a polynucleotide. One skilled in the art will appreciate that the polynucleotides, including DNA and RNA, that encode the various fragments of the peptides may be obtained from the wild-type cDNA, taking into consideration the degeneracy of codon usage, or may be engineered as desired, for example using techniques such as amplification by PCR and site-directed mutagenesis. These polynucleotide sequences may incorporate codons facilitating transcription and translation of mRNA in microbial hosts. Such manufacturing sequences may readily be constructed according to the methods well known in the art. The polynucleotides above may also optionally encode an N-terminal methionyl residue. The polynucleotides above may also optionally encode a C-terminal glycyl residue for proper amide formation. Non-peptide compounds useful in composition and methods provided herein may be prepared by art-known methods. For example, phosphate-containing amino acids and peptides containing such amino acids may be prepared using methods known in the art. See, e.g., Bartlett et al., 1986, *Bioorg. Chem.* 14: 356-377.

A variety of cell types may be used to contain and express a peptide coding sequence including, for example, bacteria, yeast, algae, insect cells, plant cells, and animal cells such as mammalian and avian cells. A variety of expression vector/host systems may be used, including, but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus (CaMV); tobacco mosaic virus (TMV) or transformed with bacterial expression vectors (e.g., Ti or pBR322 plasmid); or animal cell systems. Mammalian cells and cell lines that are useful in recombinant protein productions include, but are not limited to, VERO (African green monkey kidney) cells, HeLa cells, Chinese hamster ovary (CHO) cell lines, COS cells (such as COS-7), WI38 (human lung fibroblasts), baby hamster kidney (BHK) cells, HepG2, 3T3, RIN, Madin-Darby canine kidney epithelial (MDCK) cells, A549, PC12, K562 and 293 cells. Exemplary protocols for the recombinant expression of polypeptides are well known in the art.

Host cell strains may be chosen for a particular ability to process the expressed peptide or produce certain post-translation modifications that will be useful in providing peptide activity. Such modifications of the polypeptide include, but are not limited to, acetylation, carboxylation, glycosylation, phosphorylation, lipidation, acylation, and amidation, for example, carboxy-terminal amidation. Post-translational processing, which cleaves a "prepro" form of the polypeptide, may also be important for correct insertion, folding and/or function. Different host cells, such as CHO, HeLa, MDCK, 293, WI38, and the like, have specific cellular machinery and characteristic mechanisms for such post-translational activities, and may be chosen to ensure the correct modification and processing of the introduced foreign protein.

The NMX peptides, FNX peptides, or NMX receptor agonists, or analogs or derivatives thereof, described herein may also be produced using chemical ligation schemes known in the art, including those described, for example, in U.S. Application Publication Nos. 2003-0191291, 2003-0208046, and 2004-0115774. Chemical ligation refers to a chemoselective reaction involving the covalent joining of two chemical moieties, each of which moieties bears a mutually reactive functional group that is uniquely capable of forming a non-reversible covalent bond with the other. Unique, mutually reactive, functional groups present on the first and second components can be used to render the ligation reaction chemoselective. For example, the chemical ligation of peptides and polypeptides involves the chemoselective reaction of peptide or polypeptide segments bearing compatible unique, mutually reactive, C-terminal and N-terminal amino acid residues. Chemical ligation includes covalent ligation of (1) a first peptide or polypeptide bearing a uniquely reactive C-terminal group with (2) a second peptide or polypeptide bearing a uniquely reactive N-terminal group, where the C-terminal and N-terminal reactive groups form a non-reversible covalent bond therein between. It also includes N-terminal to N-terminal and C-terminal to C-terminal ligation. In particular, chemical ligation includes any chemoselective reaction chemistry that can be applied to ligation of unprotected peptide segments. Several different chemistries have been utilized for this purpose, examples of which include native chemical ligation, oxime forming chemical ligation, thioester forming ligation (Schnolzer et al., 1992, *Science* 256:221-225; Gieselman et al., 2001, *Org. Lett.* 3:1331-1334), thioether forming ligation (Englebretsen et al., 1995, *Tot. Leffs.* 36:8871-8874), hydrazone forming ligation (Gaertner, et al., 1994, *Bioconj. Chem.* 5:333-338), and thiazolidine forming ligation and oxazolidine forming ligation (Zhang et al., 1998, *Proc. Natl. Acad. Sci. USA* 95:9184-9189; PCT Publication No. WO 95/00846; U.S. Pat. No. 5,589,356); and Staudinger amide forming chemical ligation (Saxon et al., 2000, *Org. Lett.* 2:2141-2143).

Reaction conditions for a given ligation chemistry are generally selected to maintain the desired interaction of the peptide or polypeptide segments employed for ligation. For example, pH and temperature, water-solubility of the ligation components, ratio of the first segment to the second segment, water content and composition of the reaction mixture can be varied to optimize ligation. Addition or exclusion of reagents that solubilize the ligation segments to different extents may further be used to control the specificity and rate of the desired ligation reaction, i.e., control exposure and presentation of reactive groups by manipulating solubility of the peptide or polypeptide segments. Reaction conditions are readily determined by assaying for the desired chemoselective reaction product compared to one or more internal and/or external controls. These methodologies have proven a robust methodology for generating a native amide bond at the ligation site.

Methods useful in the synthesis of peptides and polypeptides backbones are described in, for example, U.S. Application Publication Nos. 2004-0138412 (extended native chemical ligation), 2003-0208046 (pseudo-native chemical ligation), 2005-0261473 (carboxy protection strategies for acidic C-terminal amino acids in chemical ligation to eliminate formation of unwanted side products), 2005-0064538 and 2005-0113563 (native chemical ligation with improved efficiency of ligation and chemical ligation with three or more components); in PCT Application Publication Nos. WO2004/105685 (aqueous-compatible solid phase chemical ligation using a displaceable linker) and WO2004/060925 (multiplex polymer ligation with water-soluble polymeric protecting groups and their replacement with desired adducts); and in U.S. Pat. Nos. 6,307,018 and 6,184,344 (native chemical ligation), U.S. Pat. No. 6,326,468 (solid phase native chemical ligation), U.S. Pat. No. 6,217,873 (polyoxime compounds), U.S. Pat. No. 6,174,530 (homogenous polyoxime compositions), U.S. Pat. No. 6,001,364 (hetero-polyoxime compounds), and U.S. Pat. No. 6,451,543 (lipid-matrix assisted synthesis). In general, synthesis of a peptide or polypeptide backbone by chemical ligation involves selection of suitable ligation sites that are chosen based on the ligation chemistry selected for assembling the various polypeptide backbone segments, the reversible (or cleavable) polymer attachment chemistry chosen for a given target peptide, and the particular polymer attachment sites. When native chemical ligation is employed, cysteine ligation sites are determined by scanning the target polypeptide backbone amino acid sequence for suitable naturally occurring cysteine residue. When "extended native chemical ligation" is employed, ligation sites can be selected by scanning the target polypeptide backbone amino acid sequence for suitable naturally occurring ligation site junctions that permit robust ligations. Because extended native chemical ligation is not limited to ligation at cysteine residues, any number of residues may serve as the ligation site junction. In some instances, a combination of native and extended native chemical ligation may be part of the design.

In some embodiments, native chemical ligation is used to generate part or all of the full-length polypeptide chain. Cysteines present in the naturally occurring protein or peptide backbone can be used as the chemical ligation sites. Alternatively, where a desired ligation junction is devoid of a suitable cysteine, the non-cysteine amino acid at that position can be replaced with a cysteine or a cysteine can be inserted so as to permit native chemical ligation at that site. If desired, the newly introduced cysteine can be converted to a pseudo amino acid residue corresponding to the original amino acid at that position. Formation of a pseudo amino acid by conversion of a cysteine at native chemical ligation sites is referred to "pseudo native chemical ligation." Alternatively, when the cysteine is introduced at a site for polymer protecting group modification, the side chain thiol can be exploited for the attachment of a thiol reactive water-soluble polymer construct, provided that all other cysteines in the target polypeptide that one does not wish to modify are protected. In another embodiment, extended native chemical ligation can be utilized to generate part or all of the full-length polypeptide. Peptides used for thioester-mediated ligation, such as for native chemical ligation, can be made following standard protocols as well, for example see U.S. Pat. Nos. 6,307,018 and 6,184,344.

It may be desirable to purify the NMX peptides, FNX peptides, or NMX receptor agonists, or analogs or derivatives thereof, generated by the methods described herein. Peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Purification techniques include, for example, precipitation with ammonium sulfate, PEG, antibodies, and the like; heat denaturation, followed by centrifugation; chromatography steps such as ion exchange, gel filtration, reverse phase, hydroxylapatite and affinity chromatography; isoelectric focusing; gel electrophoresis; and combinations of such and other techniques. Analytical methods particularly suited to the preparation of a pure peptide are ion-exchange chromatography, exclusion chromatography, polyacrylamide gel electrophoresis, and isoelectric focusing. A particularly efficient method of purifying peptides is reverse phase HPLC, followed by characterization of purified product by liquid chromatography/mass spectrometry (LC/MS) and Matrix-Assisted Laser Desorption Ionization (MALDI) mass spectrometry. Additional confirmation of purity is obtained by determining amino acid analysis. As is generally known in the art, it is believed that the order of conducting the various purification steps may be changed, or that certain steps may be omitted, and still result in a suitable method for the preparation of a substantially purified protein or peptide.

As used herein, the term "purified peptide" is intended to refer to a composition, isolated from other components, wherein the peptide is purified to any degree relative to its naturally obtainable state. A purified peptide therefore also refers to a peptide, free from the environment in which it may naturally occur. Generally, "purified" will refer to an NMX peptide, an FNX peptide, or an NMX receptor agonist, or an analogs or derivative thereof, that has been subjected to fractionation to remove various other components, and which composition substantially retains a biological activity. Where the term "substantially purified" is used, this designation will refer to a composition in which the peptide forms the major component of the composition, such as constituting about 50%, about 60%, about 70%, about 80%, about 90%, about 95% or more of the peptide in the composition.

There is no general requirement that the peptides always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed, utilizing an HPLC apparatus, will generally result in a greater "-fold" purification than the same technique utilizing a low pressure chromatography system. Methods exhibiting a lower degree of relative purification may have advantages in total recovery of protein product, or in maintaining the activity of the peptide. In some embodiments, a combination of anion exchange and immunoaffinity chromatography may be used to produce purified peptide compositions described herein.

The NMX peptides, FNX peptides, or NMX receptor agonists, or analogs or derivatives thereof (herein referred to as the "compounds provided"), may be administered alone or in combination with pharmaceutically acceptable carriers or excipients, in either single or multiple doses. Accordingly, pharmaceutical compositions are provided comprising a therapeutically effective amount of at least one NMX peptide, FNX peptide, or NMX receptor agonist compound, or analog or derivative thereof, or a pharmaceutically acceptable salt thereof, together with pharmaceutically acceptable diluents, preservatives, solubilizers, emulsifiers, adjuvants and/or carriers useful in the delivery of the compounds provided. Conventional description and preparation techniques for formulations are disclosed, for example, in Remington's Pharmaceutical Sciences by E. W. Martin. See also Wang et al., 1988, *Journal of Parenteral Science and Technology Technical Report No.* 10, Supp. 42:2 S.

The compounds provided may be formulated for peripheral administration, including formulation for injection, oral administration, nasal administration, pulmonary administration, topical administration, or other types of administration as one skilled in the art will recognize. Administration of the pharmaceutical compositions described herein may be via any common route so long as the target tissue is available via that route. In one embodiment, the pharmaceutical compositions may be administered via a conventional central method, e.g., intracerebroventricular. In one embodiment, the pharmaceutical compositions may be introduced into the subject by any conventional peripheral method, e.g., by intravenous, intradermal, intramuscular, intramammary, intraarticular, intraperitoneal, intrathecal, retrobulbar, intrapulmonary (e.g., term release); by oral, sublingual, nasal, buccal, anal, vaginal, or transdermal delivery, or by surgical implantation at a particular site. In some embodiments, a subcutaneous route of administration is of use. In some embodiments, mucosal delivery is exemplary. In some embodiments, the pharmaceutical compositions provided are formulated so as to be suitable for parenteral administration, e.g., via injection or infusion. In some embodiments, the compounds provided are administered in liquid, semi-solid, or solid form. The treatment may consist of a single dose or a plurality of doses over a period of time. Controlled continual release of the compounds provided is also contemplated. Parenteral administration may be carried out with an initial bolus followed by continuous infusion to maintain therapeutic circulating levels of drug product.

A form of repository or "depot" slow release preparation may be used so that therapeutically effective amounts of the preparation are delivered into the bloodstream over many hours or days following transdermal injection or delivery. Parenteral controlled release delivery can be achieved by forming polymeric microcapsules, matrices, solutions, implants and devices and administering the same parenterally or by surgical means. Examples of controlled release formulations are described in U.S. Pat. Nos. 6,368,630, 6,379,704, and 5,766,627. These dosage forms may have a lower bioavailability due to entrapment of some of the conjugates in the polymer matrix or device. See e.g., U.S. Pat. Nos. 6,379,704, 6,379,703, and 6,296,842.

When the compounds provided are delivered by inhalation, the peptides may follow the air-flow to the alveoli. Such delivery of the compounds provided may include delivery as low or ultra-low density particles, such as TECHNOSPHERES™ or as described for example in U.S. Patent Application Publication No. 2004-0170568 and U.S. Pat. No. 6,630,169.

In general, the compounds may be formulated into a stable, safe pharmaceutical composition for administration to a patient. The pharmaceutical formulations may be composed in various forms, e.g., solid, liquid, semisolid or gel. The term "solid", as used herein, is meant to encompass all normal uses of this term including, for example, powders and lyophilized formulations. The presently described formulations may be lyophilized, for example for reconstitution. Aqueous compositions generally comprise an effective amount of the compounds provided, dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated.

In some embodiments, the NMX peptides, FNX peptides, or NMX receptor agonists, or analogs or derivatives thereof contemplated herein may be prepared for administration as solutions of free base, or pharmacologically acceptable salts in water suitably mixed with a surfactant, such as hydroxypropylcellulose. Pharmaceutically-acceptable salts include the acid addition salts (formed with the free amino groups of the peptide) and which are formed with inorganic acids such as, for example without limitation, hydrochloric or phosphoric acids, or such organic acids as acetic, oxalic, tartaric, mandelic, and the like. Salts formed with the free carboxyl groups also can be derived from inorganic bases such as, for example without limitation, sodium, potassium, ammonium, calcium, or ferric hydroxides, and such organic bases as isopropylamine, trimethylamine, histidine, procaine and the like. Other pharmaceutically acceptable salts include, but are not limited to, sulfuric, citric, maleic, hydrobromide, hydroiodide, nitrate, sulfate, bisulfite, isonicotinate, lactate, salicylate, citrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Such products are readily prepared by procedures well known to those skilled in the art. Dispersions also can be prepared in glycerol, liquid polyethylene glycols, and mixtures thereof and in oils. Typically, these preparations contain a preservative to prevent the growth of microorganisms.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it. In some embodiments, the compound provided is suspended in an aqueous carrier, for example, in an isotonic buffer solution at a pH of about 3.0 to about 8.0, at a pH of about 3.5 to about 7.4, at a pH of about 3.5 to about 6.0, or at a pH of about 3.5 to about 5.0. In certain embodiments, the pH of the formulation is maintained in the range of about 3.5 to 6.5, in some embodiments from about 3.7 to about 4.3 or about 3.8 to about 4.2. In some embodiments, pH may be about 4.0.

Useful buffers include sodium citrate/citric acid, and sodium phosphate/phosphoric acid, and sodium acetate/acetic acid buffers. In certain embodiments, the buffer with the compound provided herein is an acetate buffer (for example, at a final formulation concentration of from about 1-5 to about 60 mM), a phosphate buffer (for example, at a final formulation concentration of from about 1-5 to about to about 30 mM), a glutamate buffer (for example, at a final formulation concentration of from about 1-5 to about to about 60 mM), or a citrate buffer (for example, at a final formulation concentration of from about 1-5 to about 60 mM). In some embodiments, the buffer is acetate (for example, at a final formulation concentration of from about 5 to about 30 mM).

The pharmaceutically-acceptable carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

A stabilizer may be included in the formulations of compounds provided but, and importantly, is not necessarily needed. If included, however, a stabilizer useful in the provided compositions is a carbohydrate or a polyhydric alcohol. An exemplary suitable stabilizer is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing proteins. The polyhydric alcohols include such compounds as sorbitol, mannitol, glycerol, and polyethylene glycols (PEGs), which are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. Suitable carbohydrates include without limitation galactose, arabinose, or lactose. Should the formulation be for administration to an individual with diabetes, the carbohydrate used should be one which does not have an adverse affect on the diabetic patient, i.e., the carbohydrate is not metabolized to form unacceptably large concentrations of glucose in the blood. Such carbohydrates are well known in the art as suitable for diabetics. Sucrose and fructose are suitable for use with the conjugates in non-diabetic applications (e.g., treating obesity).

In certain embodiments, if a stabilizer is included, the compound provided is stabilized with a polyhydric alcohol such as sorbitol, mannitol, inositol, glycerol, xylitol, and polypropylene/ethylene glycol copolymer, as well as various PEGs of molecular weight 200, 400, 1450, 3350, 4000, 6000, and/or 8000. Mannitol is an exemplary polyhydric alcohol in some embodiments.

Another useful feature of the lyophilized formulations provided herein is the maintenance of the tonicity of the lyophilized formulations described herein with the same formulation component that serves to maintain their stability. In some embodiments, mannitol is an exemplary polyhydric alcohol used for this purpose. In many cases, isotonic agents may be included (e.g., sugars or sodium chloride). In some cases, excipients are useful in maintenance of the overall tonicity of the compound. An excipient may be included in the presently described formulations at various concentrations. For example, an excipient may be included in the concentration range from about 0.02% to about 20% w/w, for example, between about 0.02% and 0.5% w/w, about 0.02% to about 10% w/w, or about 1% to about 20% w/w. In addition, similar to the present formulations themselves, an excipient may be included in solid (including powdered), liquid, semi-solid or gel form. Exemplary parenteral formulations may be isotonic or substantially isotonic.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide. The prevention of the action of microorganisms can be brought about by various antibacterial and antifungal agents, for example, parabens, chlorobutanol, phenol, sorbic acid, thimerosal, and the like. While the preservative for use in the pharmaceutical compositions can range from 0.005 to 1.0% (w/v), in some embodiments the range for each preservative, alone or in combination with others, is benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid.

Surfactants frequently can cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the NMX peptide, FNX peptide, or NMX receptor agonist, or analog or derivative thereof, may optionally be present in the range of about 0.001 to 0.3% (w/v) of the total formulation and include polysorbate 80 (i.e., polyoxyethylene (20) sorbitan monooleate), CHAPS® (i.e., 3-[(3-cholamidopropyl)dimethylammonio]1-propanesulfonate), Brij® (e.g., Brij 35, which is (polyoxyethylene (23) lauryl ether), poloxamer, or another non-ionic surfactant.

An exemplary vehicle for parenteral products is water. Water of suitable quality for parenteral administration can be prepared either by distillation or by reverse osmosis. Water for injection is typically the aqueous vehicle for use in the pharmaceutical formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin) and a zwitterion (e.g., an amino acid such as betaine, taurine, arginine, glycine, lysine, histidine). Additionally, polymer solutions, or mixtures with polymers provide the opportunity for controlled release of the peptide. Prolonged absorption of the injectable compositions can be brought about by the use in the compositions of agents delaying absorption (e.g., aluminum monostearate, gelatin). Such additional ingredients, of course, should not adversely affect the overall stability of the provided pharmaceutical formulation.

In some embodiments, a pharmaceutical formulation provided may contain a range of concentrations of the compound provided, e.g., between about 0.01% to about 98% (w/w), or between about 1 to about 98% (w/w), or between 80% and 90% (w/w), or between about 0.01% to about 50% (w/w), or between about 10% to about 25% (w/w). A sufficient amount of water for injection may be used to obtain the desired concentration of solution.

Exemplary pharmaceutical formulations contemplated may comprise approximately 0.01 to 1.0% (w/v), in certain cases 0.05 to 1.0% (w/v), of the compound provided, approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl, ethyl, propyl and butyl parabens and phenol. Such a preservative is generally included if the formulated peptide is to be included in a multiple use product.

The pharmaceutical compositions suitable for injectable use include sterile aqueous solutions or dispersions and sterile powders for the extemporaneous preparation of sterile injectable solutions or dispersions. In all cases, the form should be sterile and should be fluid to the extent that easy syringability exists. It is generally desirable for the compounds provided to be stable under the conditions of manufacture and storage and preserved against the contaminating action of microorganisms, such as bacteria and fungi.

Sterile injectable solutions may be prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated herein. In the case of sterile powders for the preparation of sterile injectable solutions, exemplary methods of preparation are vacuum-drying and freeze-drying techniques that yield a powder of the active ingredient plus any additional desired ingredient from a previously sterile-filtered solution thereof. In certain embodiments, the compounding procedure involves dissolution of ingredients in a specific order (e.g., preservative followed by stabilizer/tonicity agents, buffers and peptide) or dissolving at the same time. In some cases, the NMX peptide, FNX peptide, or NMX receptor agonist, or analog or derivative thereof, can be lyophilized into vials, syringes or cartridges for subsequent reconstitution. Liquid formulations provided can be filled into one or two chambered cartridges, or one or two chamber syringes.

Alternative formulations, e.g., non-parenteral, may not require sterilization. However, if sterilization is desired or necessary, any suitable sterilization process can be used in developing the peptide pharmaceutical formulation provided herein. Typical sterilization processes include filtration, steam (moist heat), dry heat, gases (e.g., ethylene oxide, formaldehyde, chlorine dioxide, propylene oxide, beta-propiolacctone, ozone, chloropicrin, peracetic acid methyl bromide and the like), exposure to a radiation source, and aseptic handling. Filtration is an exemplary method of sterilization for provided liquid formulations. The sterile filtration involves filtration through 0.45 µm and 0.22 µm (1 or 2) which may be connected in series. After filtration, the solution is filled into appropriate vials or containers.

The compounds provided herein may be provided in dosage unit form containing an amount of the compound that will be effective in one or multiple doses to treat or help in treating the psychiatric disease and/or unwanted side effect(s) of the psychiatric treatment/medication. As will be recognized by those in the field, an effective amount of therapeutic agent will vary with many factors including the age and weight of the patient, the patient's physical condition, the condition to be treated, and other factors. Appropriate dosages may be ascertained through the use of established assays for determining level of the psychiatric disorder in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, dosages of other concomitantly administered drugs, time of administration and other clinical factors. Those of ordinary skill in the art will readily optimize effective dosages and administration regimens as determined by good medical practice and the clinical condition of the individual patient.

Typically, a dosage of between about 0.001 µg/kg body weight/day to about 1000 µg/kg body weight/day may be used, but more or less, as a skilled practitioner will recognize, may be used, for example 1000 µg/kg body weight/day to 10 mg/kg body weight/day. Typical doses may contain from a lower limit of about 0.5 µg, 1 µg, 5 µg, 10 µg, 50 µg to 100 µg to an upper limit of about 100 µg, 500 µg, 1 mg, 5 mg, 10 mg, 50 mg, 100 mg or even 200 mg of the pharmaceutical compound per day. Also contemplated are other dose ranges such as 0.1 µg to 1 mg of the compound per dose. Thus, exemplary doses may be 30, 60, 120, 240, or 360 µg of the compound per dose. The doses per day may be delivered in discrete unit doses, provided continuously in a 24 hour period or any portion of that the 24 hours. The number of doses per day may be from 1 to about 4 per day, although it could be more. Dosing may be one or more times daily, or less frequently, such as one or more times weekly or one or more times monthly, and may be in conjunction with other compositions as described herein. It should be noted that the present methods and compositions are not limited to the dosages recited herein.

In some embodiments, an effective dose will typically be in the range of about 1 to 30 µg to about 5 mg/day, about 10 to 30 µg to about 2 mg/day, about 5 to 100 µg to about 1 mg/day, or about 5 µg to about 500 µg/day, for a 50 kg patient, administered in a single or divided doses. In some embodiments, dosages are between about 0.01 µg/kg/dose to about 100 µg/kg/dose. In other embodiments, the composition is formulation so as to deliver a dose of compound provided ranging from 1 µg/kg to 100 mg/kg body weight/day or at doses ranging from 0.1 mg/kg to about 50 mg/kg body weight/day. Dosages for certain routes, for example oral administration, may be increased to account for decreased bioavailability, for example, by about 5-100 fold.

Continuous delivery can be in the form of continuous infusions. Exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 µg to about 8 mg per day, whereas total dose/delivery of the pharmaceutical composition given s.c may be about 6 µg to about 16 or 24 mg per day.

The frequency of dosing will depend in part on the pharmacokinetic parameters of the agents and the routes of administration. Pharmaceutical formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as pharmacokinetic data observed in animals or human clinical trials.

The following Examples are provided to illustrate, but not limit, the invention.

EXAMPLES

Example 1

NMX peptides described herein were made by following standard polypeptide synthesis methods. Unless indicated otherwise, all exemplary NMX peptides, FNX peptides, NMX receptor agonists, or analog or derivatives thereof described herein are C-terminal amidated.

Polypeptides were synthesized on a Pioneer™ continuous flow peptide synthesizer (Applied Biosystems, Foster City, Calif.) using PAL-PEG-PS™ resin (Applied Biosystems) with a loading of 0.2 mmol/g (0.25 mmole scale). Fmoc amino acid (4.0 eq, 1.0 mmol) residues were activated using 4.0 eq HBTU, 4.0 eq of HOBT, 8.0 eq DIEA and coupled to the resin for 1 hour. The Fmoc group was removed by treatment with 20% (v/v) piperidine in dimethylformamide. Final deprotection and cleavage of the peptide from the solid support was performed by treatment of the resin with reagent B (93% trifluoroacetic acid (TFA), 3% phenol, 3% water and 1% triisopropylsilane) for 2-3 hours. The cleaved peptide was precipitated using tert-butyl methyl ether, pelleted by centrifugation and lyophilized. The pellet was re-dissolved in water (10-15 mL), filtered and purified via reverse phase HPLC using a C-18 column and an acetonitrile/water gradient containing 0.1% TFA. The purified product was lyophilized and analyzed by ESI-LC/MS and analytical HPLC and were demonstrated to be pure (>98%). Mass results all agreed with calculated values.

Alternatively, polypeptides were assembled on a Symphony® peptide synthesizer (Protein Technologies, Inc., Woburn, Mass.) using Rink amide resin (Novabiochem, San Diego, Calif.) with a loading of 0.43-0.49 mmol/g at 0.050-0.100 mmol. Fmoc amino acid (Applied Biosystems; 5.0 eq, 0.250-0.500 mmol) residues were dissolved at a concentration of 0.10 M in 1-methyl-2-pyrrolidinone. All other reagents (HBTU, 1-hydroxybenzotriazole hydrate and N,N-diisopropylethylamine) were prepared as 0.55 M dimethylformamide solutions. The Fmoc protected amino acids were then coupled to the resin-bound amino acid using, HBTU (2.0 eq, 0.100-0.200 mmol), 1-hydroxybenzotriazole hydrate (1.8 eq, 0.090-0.18 mmol), N,N-diisopropylethylamine (2.4 eq, 0.120-0.240 mmol) for 2 hours. Following the last amino acid coupling, the peptide was deprotected using 20% (v/v) piperidine in dimethylformamide for 1 hour. Once peptide sequence is completed, the Symphony® peptide synthesizer is programmed to cleave the resin. Trifluoroacetic acid (TFA) cleavage of the peptide from resin was carried out using a reagent mixture composed of 93% TFA, 3% phenol, 3% water and 1% triisopropylsilane. The cleaved peptide was precipitated using tert-butyl methyl ether, pelleted by centrifugation and lyophilized. The pellet was dissolved in acetic acid, lyophilized and then dissolved in water, filtered and purified via reverse phase HPLC using a $C_{18}$ column and an acetonitrile/water gradient containing 0.1% TFA. Analytical HPLC was used to assess purity of peptide and identity was confirmed by LC/MS and MALDI-MS.

Example 2

Animal behavior assays were performed to test for anxiolytic and antipsychotic effects of FN-38 (SEQ ID NO:5) administration. The behavioral assays performed use art-accepted, animal models that demonstrate properties characteristic of the respective clinical condition (e.g., anxiety, schizophrenia, obsessive-compulsive disorder) and hence, show face validity. These specific behavioral tests are known to be sensitive to anxiolytic or antipsychotic drugs. For these assays, FN-38 was administered to mice at doses ranging from 0.1 to 10 mg/kg, intraperitoneally, and their performance in the assay was assessed.

Stress-induced Hyperthermia

Body temperature and emotionality are correlated in humans and stress commonly induces an increase in body temperature (hyperthermic response) in rodents. The thermic response to stress is commonly used as an indication of enhanced emotionality or anxiety in rodents and stress-induced hyperthermia (SIH) in mice is considered to have predictive validity for certain human anxiety/stress disorders. The SIH assay assesses the effect of anxiolytics or test agents on SIH and measures the intrinsic effects of these drugs on core body temperature of the animal. See, for example, Zethof et al., 1994, *Physiol. Behav.* 55:109-115. Anxiolytics blunt the increase in body temperature, or hyperthermic response, following stress exposure. Buspirone is a partial 5-HT1A agonist and a known anxiolytic agent. The animals were treated with FN-38 (0.1, 1.0 or 10 mg/kg) or control agents (vehicle (water) or 15 mg/kg buspirone) 60 minutes before the assay. Mice were subjected to two sequential rectal temperature measurements ten minutes apart. The stress from the first measurement induces hyperthermia which was measured by the second temperature measurement. The difference between the two temperatures (Delta Temperature) was the stress-induced hyperthermia. Results of this assay are shown in FIG. 1 where * is P<0.05 vs. vehicle control. As shown in FIG. 1, administration FN-38 at 10 mg/kg, like that of the anxiolytic positive control, buspirone, blunted the SIH response. The SIB test results demonstrate the anxiolytic activity of FN-38 administration.

Marble Burying

Marble burying is used as a model for both anxiety and obsessive-compulsive disorder. See, for example, Chaki et al., 2003, *J. Pharmacol. Exp. Ther.* 304:818-826. Anxiolytics suppress marble burying activity. Benzodiazepine chlordiazepoxide (CDP) is a known anxiolytic agent. Mice were injected with the test agent (FN-38 (SEQ ID NO:5) at 0.1, 1.0 or 10 mg/kg, 15 mg/kg CDP, or vehicle (water)) 15-30 minutes prior to the test. Mice were then placed individually in clean cages containing 5-cm of hard wood bedding and 20 marbles spaced evenly in rows of five. The number of marbles buried in 30 minutes was recorded. Results of this assay are shown in FIG. 2 where * is P<0.05 vs. vehicle control. As shown in FIG. 2, administration of FN-38 at 10 mg/kg, like that of the anxiolytic positive control, CDP at 15 mg/kg, reduced the number of marbles buried. These reductions in marble burying were statistically significant. The marble burying assay results demonstrate the anxiolytic activity and the anti-obsessive compulsive activity of FN-38 administration.

Phencyclidine (PCP)-induced Locomotion

The PCP-induced locomotion test is used with open field activity chambers and measures locomotion, rearing, and stereotypic activity under amphetamine/PCP-induced conditions. The test has predictive validity for some antipsychotic drugs that normalize the hyperactivity and stereotypic behavior seen with amphetamine and PCP. See, for example, Williams et al., 2006, *Prog. Neuropsychopharmacol. Biol. Psychiatry*, 30:239-243. Mice were injected with the test agent (FN-38 (SEQ ID NO:5) at 0.1, 1.0 or 10 mg/kg, or vehicle (water)) 15-30 minutes prior injection with 5 mg/kg PCP. The animals were then placed in the center of an open field and activity was recorded for 60 minutes. Results of this assay with FN-38 at 10 mg/kg are shown in FIG. 3. As shown in FIG. 3, PCP induced a characteristic response of hyper-locomotion in vehicle pre-treated animals. Administration of FN-38 significantly reduced this hyper-locomotion response as seen by a reduction in the total distance traveled across all types assessed (total, central, and peripheral) in the PCP-induced locomotion test. The PCP-induced locomotion test results demonstrate the antipsychotic activity of FN-38 administration.

Prepulse Inhibition

The prepulse inhibition (PPI) test measures the reflex response to externally applied auditory stimulation (acoustic startle response) and is related to the deficiency in sensory-motor gating capacity seen in schizophrenia. The acoustic startle reflex is a very basic response to strong exteroceptive stimuli and is widely used to assess sensorimotor reactivity in animals and humans. A weak auditory stimulus (prepulse, 74-82 dB) given prior to the strong acoustic stimulus (120 dB) blunts the startle response. This blunting of the startle response is referred to as prepulse inhibition. See, for example, Conti et al., 2005, *Behavioral Neuroscience* 119: 1052-1060. Antipsychotics increase the ability of the prepulse stimulus to blunt the startle response to the strong stimulus. Some psychotomimetic agents, such as phencyclidine (PCP) and ketamine, can actually reduce the percent prepulse inhibition and stimulate a psychotic-like state in animals, which can be antagonized by antipsychotic agents.

Mice were injected with the test agent (FN-38 (SEQ ID NO:5) at 0.1, 1.0 or 10 mg/kg, or vehicle (water)) 15 prior to the test or with haloperidol at 1 mg/kg or vehicle (10% DMSO) 30 minutes prior to the test. The mice were placed into an animal holder and the holder placed onto a transducer platform in an acoustic chamber. A weak auditory stimulus (prepulse) of 74, 78 and 82 dB was given prior to the strong acoustic stimulus of 120 dB. The amount of the animal's "reaction" to the strong stimulus was recorded. Results of the PPI assay with FN-38 at 10 mg/kg are shown in FIG. 4. As shown in FIG. 4, administration of FN-38 at 10 mg/kg, like that of the antipsychotic positive control haloperidol, increased the percent of prepulse inhibition at the 78 and 82 dB prepulse stimulatory intensity levels. Haloperidol is a dopamine receptor antagonist and a first generation antipsychotic agent. The PPI test results support the antipsychotic effects of FN-38 administration.

All patents and other references cited herein are indicative of the level of skill of those skilled in the art to which the references pertain, and are incorporated by reference in their entireties and for all purposes, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms to describe distinct subject matter. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the claims.

In addition, where features or aspects of the invention are described in terms of Markush groups or other grouping of alternatives, those skilled in the art will recognize that the invention is also thereby described in terms of any individual member or subgroup of members of the Markush group or other group. It is specifically contemplated that each member of the Markush group should be considered separately, thereby comprising another embodiment, and the Markush group is not to be read as a single unit.

Also, unless indicated to the contrary, where various numerical values are provided for embodiments, additional embodiments are described by taking any two different values as the endpoints of a range. Such ranges are also within the scope of the described invention.

What is claimed is:

1. A method for treating schizophrenia in a human in need thereof comprising administering to the human a therapeutically effective amount of a peptide comprising the amino acid sequence of (SEQ ID NO: 5)
FLFHYSKTQKLGKSNVVEELQSPFASQSRGYFLFRPRN-NH$_2$ to treat the schizophrenia.

2. The method of claim 1, further comprising administering to the human a therapeutically effective amount of a second generation antipsychotic.

3. A method for treating schizophrenia in a human in need thereof comprising administering to the human a therapeutically effective amount of a peptide that has at least 90% sequence identity to the peptide comprising the amino acid sequence of (SEQ ID NO: 5)
FLFHYSKTQKLGKSNVVEELQSPFASQSRGYFLFRPRN-NH$_2$ to treat the schizophrenia.

4. The method of claim 3, further comprising administering to the human a therapeutically effective amount of a second generation antipsychotic.

* * * * *

UNITED STATES PATENT AND TRADEMARK OFFICE
CERTIFICATE OF CORRECTION

PATENT NO. : 8,309,522 B2
APPLICATION NO. : 12/524903
DATED : November 13, 2012
INVENTOR(S) : Laugero et al.

Page 1 of 1

It is certified that error appears in the above-identified patent and that said Letters Patent is hereby corrected as shown below:

On the Title Page:
Item (54), and in the Specification, Column 1, Line 2, in the Title, before "PSYCHIATRIC" delete "TREATING"
Item (75), Inventors, delete "Corte Madero, CA" and insert --Corte Madera, CA--

Signed and Sealed this
Third Day of December, 2013

Margaret A. Focarino
*Commissioner for Patents of the United States Patent and Trademark Office*